(12) United States Patent
Mosberg et al.

(10) Patent No.: US 7,432,242 B2
(45) Date of Patent: Oct. 7, 2008

(54) INHIBITORS OF RGS PROTEINS

(75) Inventors: Henry I. Mosberg, Ann Arbor, MI (US); Richard R. Neubig, Ann Arbor, MI (US); Yafei Jin, Dallas, TX (US); Hauiling Zhong, Lake Hiawatha, NJ (US); Roger Sunahara, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 277 days.

(21) Appl. No.: 10/365,840

(22) Filed: Feb. 13, 2003

(65) Prior Publication Data

US 2004/0053821 A1    Mar. 18, 2004

Related U.S. Application Data

(60) Provisional application No. 60/357,418, filed on Feb. 15, 2002.

(51) Int. Cl.
*A61K 38/12* (2006.01)
(52) U.S. Cl. ......................................................... 514/9
(58) Field of Classification Search ................. None
See application file for complete search history.

(56) References Cited

U.S. PATENT DOCUMENTS

| | | |
|---|---|---|
| 4,501,728 A | 2/1985 | Geho et al. |
| 4,737,323 A | 4/1988 | Martin et al. |
| 4,837,028 A | 6/1989 | Allen |
| 5,051,448 A | 9/1991 | Shashoua |
| 5,169,862 A | 12/1992 | Burke, Jr. et al. |
| 5,192,746 A | 3/1993 | Lobl et al. |
| 5,539,085 A | 7/1996 | Bischoff et al. |
| 5,559,103 A | 9/1996 | Gaeta et al. |
| 5,576,423 A | 11/1996 | Aversa et al. |
| 5,607,691 A | 3/1997 | Hale et al. |
| 5,929,207 A | 7/1999 | Horvitz et al. |
| 6,069,296 A | 5/2000 | Horvitz et al. |
| 6,274,362 B1 | 8/2001 | Hodge et al. |

OTHER PUBLICATIONS

Zheng et al., Trends Biochem. Sci., vol. 24, pp. 411, 1999.*
Zhong et al. Journal of Pharmacol. and Exp. Ther., vol. 297, pp. 837, 2001.*
DeVries et al., Ann Rev Pharmacol 40:235 [2000].
Ross and Wilkie, Ann Rev Biochem 69:795 [2001].
DeVries et al., Proc Natl Acad Sci U S A 92: 11916 [1995].
Zheng et al., Trends Biochem. Sci., 24:411 [1999].
Zhong and Neubig, Journal of Pharmacol. and Exp. Ther., 297:837 [2001].
Clark et al., Nature, Aug. 3, 2000;406(6795):532-5.
Coleman and Sprang, J. Biol. Chem. 274:16669 [1999].
Eldred et al. (J. Med. Chem., 37:3882 [1994].
Ku et al. (J. Med. Chem., 38:9 [1995].
Berman et al., J. Biol. Chem., 271:27209 [1996].
Berman et al., Cell 86:445 [1996].
Wise and Milligan, J. Biol. Chem., 272:24673 [1997].
Wieland et al., Methods Enzymol. 237:3 [1994].

* cited by examiner

*Primary Examiner*—Christopher R. Tate
*Assistant Examiner*—Roy Teller
(74) *Attorney, Agent, or Firm*—Casimir Jones, S.C.

(57) ABSTRACT

The present invention relates to novel inhibitors of G-protein signaling. In particular, the present invention provides peptide inhibitors of G protein signaling proteins and methods of using such inhibitors to modulate physiological effects of G protein signaling. The present invention thus provides novel drug targets for a variety of pathologies mediated by defects in G-protein signaling.

13 Claims, 22 Drawing Sheets

Figure 1A

Examples of the Functional Effects Exerted by Members of RGS Subfamilies in Different Systems

| RGS | Size (aa) | Non-RGS Domains | Tissue Distribution | Examples of Functional Effects |
|---|---|---|---|---|
| Dedicated/small RGS | | | | |
| RGS1 | 196h | Short N-terminal domain; function not determined | Lymphocytes | Down-regulates chemotaxis of lymphocytes to chemokines (Moratz et al., J. Immunol, 164:1829 [2000]) *b* ; modulates postsynaptic GIRK currents in neurons and atrial cells (Doupnik et al., PNAS 94:10461 [1997]) |
| RGS2 | 211h | | Ubiquitous | Suppresses mGluR1a- mediated inhibition of M- type potassium currents in sympathetic neurons (Kammermeier and Ikeda, Neuron 22:819 [1999]); inhibits muscarinic acetylcholine receptor-mediated MAP kinase activation (Ingi et al., J. Neurosci, 18:7178 [1998]). Knockout mice show reduced T cell proliferation and IL-2 production, increased anxiety responses, and decreased male aggression (Oliveira-Dos-Santos et al., PNAS 97:12272 [2000]). Functions are also implied by its dynamic regulation in osteoblasts as well as by its increase in expression in response to stimuli such as elevated cAMP levels, PKC, neuronal activity, and certain psychoactive agents (Ingi et al., 1998, supra; Burchett et al., J. Neurochem., 72:1529 [1999]). |
| RGS8 | 180r | | Brain | Accelerates GIRK currents (Saitoh et al., J. Biol. Chem., 274:9899 [1999]); attenuate receptor-mediated Ca 2 1 channel inhibition in HEK293 cells *b* |
| RGS10 | 173h | | Brain | |
| RGS13 | 159h | | Lung | |
| RGS18 | 235m | | Bone marrow,* lung, spleen, fetal liver | Attenuates angiotensin receptor-mediated IP production and M1 muscarinic receptor-stimulated gene activation via cAMP-responsive element (Park et al., J. Biol. Chem., 276:915 [2000]) |
| RGS4 | 205r | Short N-terminal domain with amphipathic helices important for membrane association | Brain, heart | Down-regulates chemotaxis of lymphocytes to chemokines *b* ; modulates GIRK currents in neurons and atrial cells (Doupnik et al., 1997, supra); inhibits translocation of the glucose transporter (Glut4) in adipocytes (Kanzaki et al., J. Biol. Chem., 275:7167 [2000]) |
| RGS5 | 181m | | Brain, heart, lung, Muscle | |
| RGS16 *c* | 201m | | Liver, pituitary | Attenuates platelet-activating factor-induced responses in CHO cells *b* ; inhibits translocation of Glut4 in adipocytes (Kanzaki et al., 2000, supra); potential function is |

Figure 1B

| | | | |
|---|---|---|---|
| | | | suggested by increased expression of RGS16 in response to genotoxic stress (Buckbinder et al., PNAS 94:7868 [1997]) and by its possible mutation contributive to certain forms of retinitis pigmentosa (Bessant et al., J. Med. Genet., 37:384 [2000]) |
| | | | Dedicated RGS |
| RGS3 | 519h | Long N- terminal domain, function not determined | Kidney | Down- regulates chemotaxis of lymphocytes to chemokines *b* ; modulates postsynaptic GIRK currents in neurons and atrial cells (Doupnik et al., 1997, supra); reduces tubular migration in kidney (Gruning et al., Am. J. Physiol., 276:F535 [1999]); attenuates receptor- mediated Ca 2 1 channel inhibition in HEK293 cells *b* |
| C29H12.3 | 284e | (2 RGS domains) | | |
| | | | | DEP/ GGL RGS |
| RGS6 | 567h | N- terminal DEP/ GGL | Brain | |
| RGS7 | 469h | | Brain (neocortex*, hippocampus*, and certain nuclei*) | Up- regulation of RGS7 suggests a role in tumor necrosis factor- induced changes in the brain (Benzing et al., Nat. Med., 5:913 [1999]); interacts with polycystin (Kim et al., PNAS 96:6371 [1999]) |
| RGS9- 1 | 484h | | Retina | Accelerates recovery of rod vision (Chen et al., Nature 403:557 [2000]) |
| RGS9- 2 | 674h | | Brain (especially striatum*) | Decreases Gi/ o coupled m-opioid receptor response in vitro (Rahman et al., J. Neurosci., 19:2016 [1999]) |
| RGS11 | 467h | | Brain | |
| EGL- 10 | 555e | | | Regulates egg- laying behavior (Koelle and Horvitz, Cell 84:115 [1996]) |
| EGL- 16 | 474e | | | Inhibits endogenous Gq/ G11 activity in COS- 7 cells (Hajdu- Cronin et al., Genes Dev., 13:1780 [1999]) |
| | | | | Cysteine string RGS |
| GAIP | 217h | N- terminal cysteine string | Heart, liver, lung | Possible role in the regulation of vesicular trafficking (De Vries et al., PNAS 95:12340 [1998]) |
| Ret- RGS1 | 374b | | Retina | |
| RGS- Z1 | 217h | | Brain | |

Figure 1C

| | | | |
|---|---|---|---|
| RGS17 d | 210c | | Not determined |
| | | | GoLoco RGS |
| RGS12 | 1387r | Raf-I; GoLoco; PDZ/PTB | Brain, lung, liver |
| RGS14 | 547m | Raf-I, GoLoco | Brain, lung, spleen |
| | | | Axin RGS |
| Axin | 832r | GSK-catenin binding; DIX | Ubiquitous |
| Conductin | 840m | | Brain, liver, lung |
| | | | PDZRhoGEF RGS |
| P115RhoGEF | 913h | DH/PH | Ubiquitous |
| LscRhoGEF | 914m | DH/PH | Ubiquitous |
| PDZRhoGEF | 1522h | DH/PH; PDZ | Ubiquitous |
| GRK RGS | | | |
| GRK2 e | 689h | Kinase/ GRK; Gβγ binding | Brain |
| GRK3 e | 688h | | Brain |
| | | | RasGAP RGS |
| Sst2 | 698y | RasGAP | |
| FLBA | 719y | | |
| | | | AKAP RGS |
| D- AKAP2 | 372m | PKA anchoring | Ubiquitous |

Notes column (right side):
- Inhibits mediated serum response factor activation in NIH3T3 cells b
- Attenuates IL- 8 receptor- mediated MAP kinase activation and M1 acetylcholine receptor- stimulated c- fos SRE activation (Cho et al., Mol. Pharmacol. 58:569 [2000])
- Generally viewed as a tumor suppressor (Peifer and Polakis, 287:1606 [2000])
- Inhibits Gα-mediated activation of PLC in HEK293 cells (Carman et al., J. Biol. Chem., 274:34483 [1999])
- Inhibits pheromone response (Dohlman et al., Mol. Cell. Biol. 16:5194 [1996])

MAP, mitogen- activated protein; PKA, protein kinase A; PKC, protein kinase C; IP, inositol phosphate; CHO, Chinese hamster ovary; SRE, serum response element a A letter following size [amino acids (aa)] indicates the species from which that RGS is characterized: h, human; r, rat; m, mouse; b, bovine; c, chicken; y, yeast; e, C. elegans. Note that homologs or orthologs from species other than listed for many of the RGS members have also been identified but are not shown.b See De Vries et al. (2000) for appropriate or more references.c The protein A28- RGS14p reported by Buckbinder et al. (1997) is RGS16, not RGS14.d RGS17 has also been called RGSZ2 by S. A. Barker and E. M. Ross (unpublished, GenBank accession number NM_ 019958).e GRK1, GRK4, GRK5, and GRK6 have also been identified as having N- terminal RGS domains (see Siderovski et al., 1996).

Figure 5
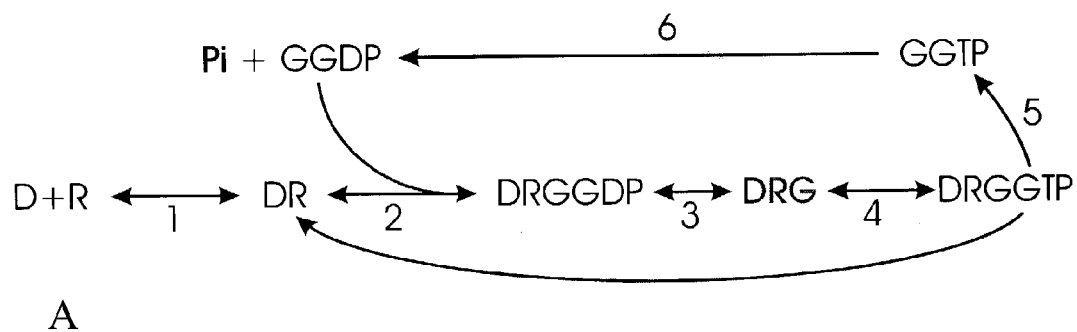
A
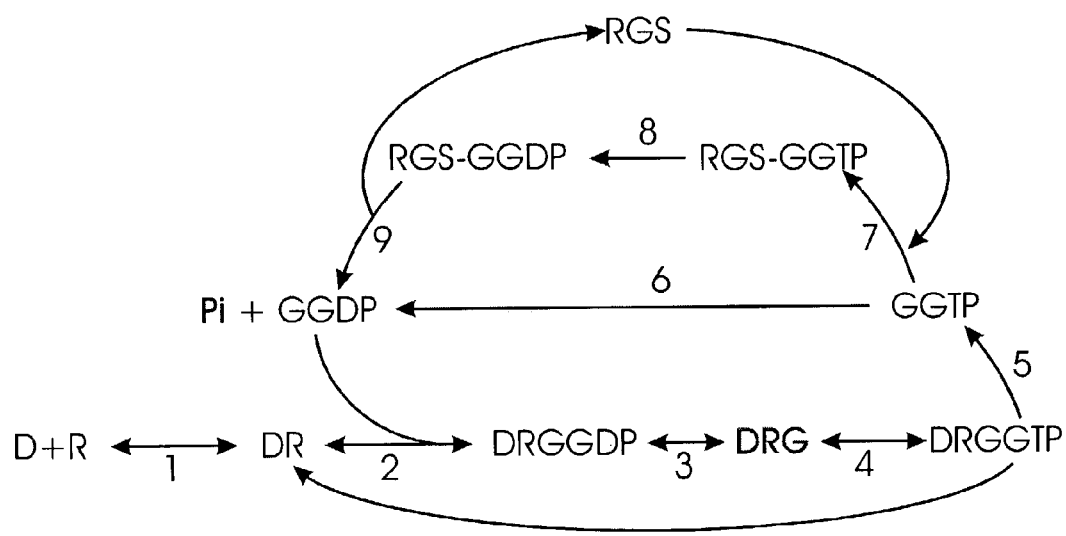
B

Figure 12A

| Name (synonym) | Class[a] | Gα targets of RGS-box | Basal CNS expression pattern[b] | Known modulators of CNS expression |
|---|---|---|---|---|
| RGS2 (G0S8) | B, R4 | Gαq>>Gαi (Gαs?) | Cerebral cortex; striatum; hippocampus; amygdala; thalamic & hypothalamic nuclei; pontine, interpeduncular, & dorsal raphe nuclei | ↑ in amygdala, cortex, hippocampus, and striatum by electroconvulsive seizure; ↑ in hippocampus by NMDA-receptor-mediated neuronal excitation; ↑ in striatum by amphetamine, cocaine, methamphetamine, haloperidol, raclopride, risperidone; ↑ in forebrain by rapid kindling |
| RGS3 | B, R4 | Gαi, Gαq | Principal thalamic relay nuclei, white matter | ↑ in striatum by amphetamine |
| RGS4 | B, R4 | Gαi, Gαo, Gαq, Gαz | Cerebellar Purkinje cell layer; cortex; amygdala; striatum; thalamus; pyramidal cell layer of hippocampus | ↑ in locus coeruleus and ↓ in paraventricular nucleus and pituitary by chronic unpredictable stress or corticosterone; ↑ in lumbar spinal cords by chronic neuropathic pain; ↓ in prefrontal cortex in schizophrenia; ↑ in hippocampus and ↓ in forebrain by rapid kindling |
| RGS5 | B, R4 | Gαi, Gαo, Gαq | Hypothalamic paraventricular and supraoptic nuclei; basomedial | ↑ in striatum by acute (but not chronic) amphetamine administration; ↓ in cerebral capillaries in |

Figure 12B

| | | | | |
|---|---|---|---|---|
| | | | amygdala; glia; brain capillary endothelium; choriod plexus | cerebral capillaries in stroke-prone spontaneously hypertensive rats |
| RGS7 | C, R7 | Gαo | Cerebral neocortex; pyriform cortex; thalamus; hypothalamus; hippocampus; amygdala; cerebellar granule cell layer; retina | ↑ in primary cortical neuronal cultures by phorbol ester treatment; ↑ in brain in mice treated with lipopolysaccharide (LPS) or tumor necrosis factor-alpha (TNFα) |
| RGS9-1 (RGS9S) | C, R7 | Gαt | Retina (rod and cone photoreceptors) | |
| RGS9-2 (RGS9L) | C, R7 | Gαi, Gαo | Striatum; hypothalamic nuclei | ↑ in striatum in Parkinson's disease; ↓ in striatum by amphetamine or chronic morphine administration |
| RGS10 | R12 | Gαi, Gαo, Gαz | Parietal neocortex layers II & III; dentate gyrus granule cells; dorsal raphe | ↓ in dentate gyrus and parietal neocortex in electroconvulsive seizure |
| RGS12 | D, R12 | Gαi, Gαo | Cerebellum; cerebral cortex & medulla; striatum; hippocampus; amygdala; occipital pole; frontal & temporal lobes | |
| RGS14 | D, R12 | Gαi, Gαo | Similar to RGS2, but at lower expression levels | |
| RGS16 (RGS-r) (A28-RGS14p) | B, R4 | Gαi, Gαo, Gαq | Retina; thalamic midline/intralaminar and principal relay nuclei; hypothalamic suprachiasmatic nucleus | |

Figure 12C

| | | | | |
|---|---|---|---|---|
| RGS19 (GAIP) | A, RZ | Gαi, Gαo, Gαz | Similar to RGS2, but at lower expression levels | |
| RGS20 (RGS-Z1) (RET-RGS) | A, RZ | Gαz | Retina; cerebellum; cerebral cortex; striatum; hippocampus; amygdala; frontal & temporal lobes | |

[a] Based on alternative sub-family nomenclatures proposed by Zheng et al.[90] and Wilkie and Ross[91]

[b] Based predominantly on *in situ* hybridization studies of the rat CNS by Gold et al.[39], Ingi et al.[43], and Grafstein-Dunn et al.[75]

Figure 13

| Tissue | RGS | Receptor | Response |
|---|---|---|---|
| Pancreatic acinar cells | 4, 1, 16<br>2 | Musc>CCK<br>Musc=CCK | Intracellular calcium<br>"         " |
| A10 vascular smooth muscle | 3<br>5 | Muscarinic (m3)<br>Angiotensin (AT1) | ERK2<br>phosphorylation |
| Dorsal root ganglion neurons | 4<br>GAIP<br>12 | $\alpha_2$ AR<br>$\alpha_2$ AR<br>GABA$_B$ | Calcium channel (Gi)<br>"         " (Go)<br>"         " (Go) |

INHIBITORS OF RGS PROTEINS

This application claims priority to U.S. provisional patent application Ser. No. 60/357,418, filed Feb. 15, 2002.

This invention was made with government support under Grants No. GM39561 and DA03910 awarded by the National Institutes of Health. The Government has certain rights in the invention.

FIELD OF THE INVENTION

The present invention relates to novel inhibitors of regulators of G-protein signaling and methods of screening for such inhibitors. In particular, the present invention provides peptide inhibitors of regulator of G-protein signaling proteins and methods of using such inhibitors to modulate physiological effects of G protein and receptor signaling.

BACKGROUND OF THE INVENTION

G proteins are a large and diverse family of proteins. Defects in G protein signaling are implicated in a diverse variety of physiological responses to pharmaceuticals as well as in disease.

G proteins play important roles in the regulation of cell growth, differentiation, and oncogenic transformation. Agonists acting at G protein couples receptors have been implicated as oncogenes (for a review, See e.g., Gudermann et al., Nauyn-Schmiedeberg's Arch. Pharmacol., 361:345 [2000]). Research indicates that an irregularity in any GPCR pathway component can cause a physiological defect (Meij, Mol. Cell. Biochem. 157:31 [1996]). For example, mutations in components of the cell signaling cascade as well as alterations in the expression pattern of these components may result in abnormal activation of leukocytes and lymphocytes, leading to the tissue damage and destruction seen in autoimmune diseases such as rheumatoid arthritis, biliary cirrhosis, hemolytic anemia, lupus erythematosus, and thyroiditis. T cell activation is also a G protein regulated process (Aussel et al., J. Immunol. 140:215 [1988]).

Irregularities in G protein signaling also have a role in abnormal cell proliferation. Cyclic AMP stimulation of brain, thyroid, adrenal, and gonadal tissue proliferation is regulated by G proteins. Mutations in $G_\beta$ subunits have been found in growth-hormone-secreting pituitary somatotroph tumors, hyperfunctioning thyroid adenomas, and ovarian and adrenal neoplasms (Spiegel, J. Inher. Metab. Dis. 20:113 [1997]).

Genetic disorders caused by loss or gain of function mutations in G, subunits include Albright hereditary osteodystrophy, pseudohypoparathyroidism type Ia with precocious puberty, McCune-Albright syndrome, and congenital night blindness (Spiegel, supra). GPCR mutations are responsible for many diseases including color blindness, retinitis pigmentosa, congenital night blindness, nephrogenic diabetes insipidus, familial adrenocorticotropic hormone (ACTH) resistance, hypergonadotropic ovarian dysgenesis, familial male precocious puberty, male pseudohermaphroditism, sporadic hyperfunctional thyroid nodules, familial nonautoimmune hyperthyroidism, familial hypothyroidism, familial hypocalciuric hypercalcemia/neonatal severe primary hyperparathyroidism, familial hypoparathyroidism, congenital bleeding, Hirschsprung disease, Jansen metaphyseal chondrodysplasia, and familial growth hormone deficiency (Spiegel, supra). A G-protein controlled pathway, the β-adrenoreceptor/adenylate cyclase pathway, appears to be desensitized in heart failure (Meij, supra).

G protein-coupled receptors (GPCRs) play a major role in signal transduction and are targets of many therapeutic drugs. The regulator of G protein signaling (RGS) proteins form a recently identified protein family (See e.g., DeVries et al., Ann Rev Pharmacol 40:235 [2000]; Ross and Wilkie, Ann Rev Biochem 69:795 [2001]). RGS proteins strongly modulate the activity of G proteins. Their best-known function is to inhibit G protein signaling by accelerating GTP hydrolysis (GTPase activating protein (GAP)) thus turning off G protein signals. RGS proteins also possess non-GAP functions, through both their RGS domains and various non-RGS domains and motifs (e.g., GGL, DEP, DH/PH, PDZ domains and a cysteine string motif). They are a highly diverse protein family, have unique tissue distributions, are strongly regulated by signal transduction events, and play diverse functional roles in living cells.

Thus, effective modulators of G-protein signaling for use in the treatment of G-protein mediated pathologies are needed.

SUMMARY OF THE INVENTION

The present invention relates to novel inhibitors of regulators of G-protein signaling and methods of screening for such inhibitors. In particular, the present invention provides peptide inhibitors of regulator of G-protein signaling proteins and methods of using such inhibitors to modulate physiological effects of G protein and receptor signaling.

Accordingly, in some embodiments, the present invention provides a composition comprising a peptide that inhibits the GTPase acceleration activity of an RGS protein. In some embodiments, the peptide is a constrained peptide. The present invention is not limited to a particular peptide. Any suitable constrained peptide may be utilized including, but not limited to

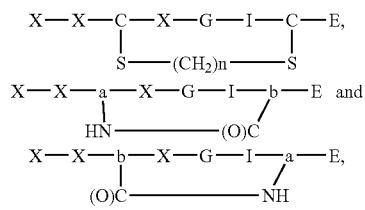

wherein X is any amino acid, a is an amino acid with an amine side chain and b is an amino acid with a carboxyl side chain. For example, in some embodiments, the peptide comprises (SEQ ID NO: 13)

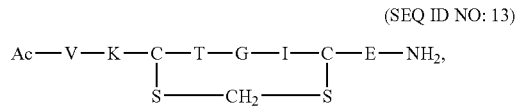

(SEQ ID NO: 14)

(SEQ ID NO: 15)

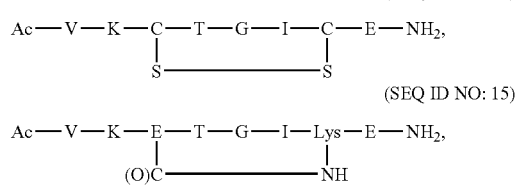

-continued

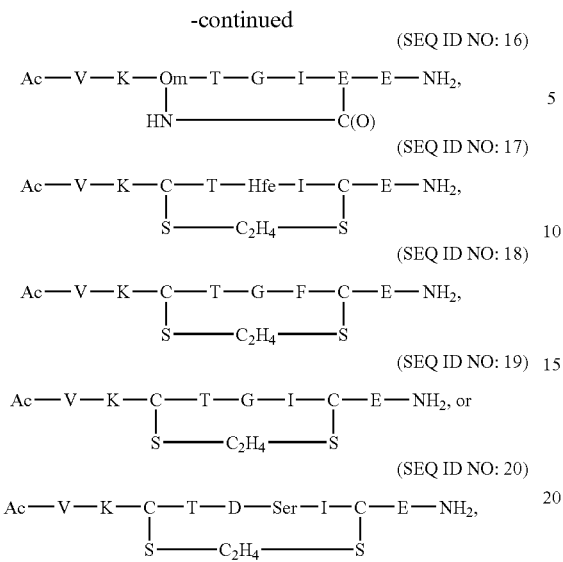

where Ac is Acetyl (denotes here acetylated α amine of the N-terminal Valine residue), $A_2bu$ is 1,4 diamino butanoic acid, $A_2pr$ is 1,3 diamino propanoic acid, Suc is succinyl (denotes succinylated α amine of the N-terminal residue), Hfe is homophenylalanine, —OH is a free carboxylic acid group at the carboxy terminal, —$NH_2$ is a carboxamide group at the carboxy terminal, Orn is ornithine, CH2 is a methyl group, and $C_2H_4$ is an ethyl group. In some embodiments, the RGS protein is a $G_i$ coupled RGS protein. In other embodiments, the RGS protein is a $G_o$ coupled RGS protein. In further embodiments, the RGS protein is a $G_q$ coupled RGS protein. In still further embodiments, the RGS protein is a $G_s$ coupled RGS protein. In yet other embodiments, the protein is a $G_{12/13}$ coupled RGS protein. In some embodiments, the RGS protein is selected from the group including, but not limited to, Family A, B, C, D, and F RGS proteins. In some embodiments, the RGS protein is selected from the group including, but not limited to, RGS4 and RGS8.

The present invention also provides a method of inhibiting the GTPase accelerating activity of an RGS protein, comprising: providing at least one RGS protein; and at least one test compound; and contacting the RGS protein and the test compound under conditions such that the test compound inhibits the GTPase acceleration activity of the RGS protein. In some embodiments, the test compound is a peptide. In some preferred embodiments, the peptide is a constrained peptide. In some embodiments, the RGS protein is a $G_i$ coupled RGS protein. In other embodiments, the RGS protein is a Go coupled RGS protein. In further embodiments, the RGS protein is a $G_q$ coupled RGS protein. In still further embodiments, the RGS protein is a $G_s$ coupled RGS protein. In yet other embodiments, the protein is a $G_{12/13}$ coupled RGS protein. In some embodiments, the RGS protein is selected from the group including, but not limited to, Family A, B, C, D, and F RGS proteins. In some embodiments, the RGS protein is selected from the group including, but not limited to, RGS4 and RGS8. In some embodiments, the peptide comprises

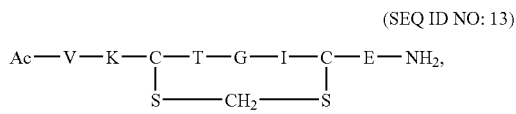

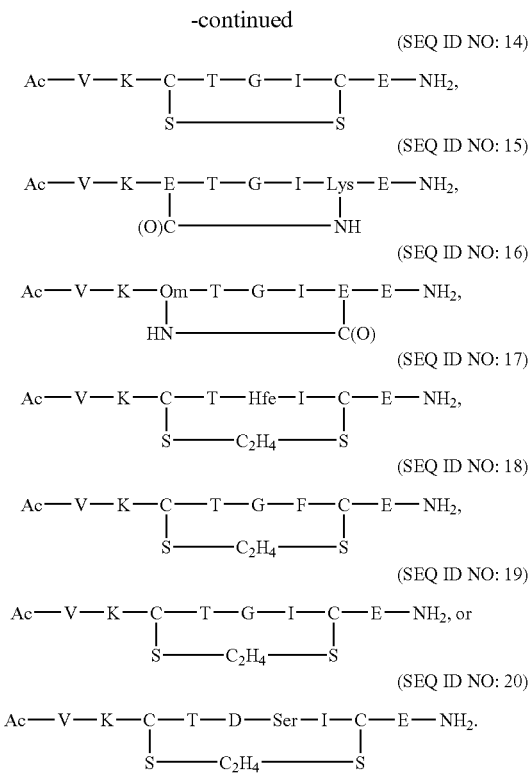

In some embodiments, the test compound inhibits the binding of the RGS protein to a G protein. In some embodiments, the peptide is fluorescently labeled. In some embodiments, the RGS protein is in a cell.

The present invention additionally provides a method, comprising: providing a G protein; a cell membrane expressing a coupled G protein receptor coupled to the G protein; at least one RGS protein; GTPγS; and at least one test compound; and incubating said membrane with said coupled G protein receptor, said G protein, said test compound, said at least one RGS protein, and said GTPγS under conditions such that said coupled G protein receptor is stimulated, and wherein said GTPγS binds to said G protein; and determining the amount of GTPγS bound to the G protein. In some embodiments, the coupled G protein receptor is selected from the group including, but not limited to, a $G_i$ coupled G protein receptor, a $G_q$ coupled G protein receptor, a $G_s$ coupled G protein receptor, a $G_{12/13}$ coupled G protein receptor and a $G_o$ coupled G protein receptor. In some embodiments, the method further comprises the step of determining the amount of GTPγS bound to the coupled G protein receptor in the absence of the test compound. In some embodiments, the RGS protein is selected from the group including, but not limited to, $G_i$ coupled RGS proteins, $G_s$ coupled RGS proteins, $G_q$ coupled RGS proteins, $G_{12/13}$ coupled RGS proteins and $G_o$ coupled RGS proteins. In some embodiments, the test compound is a peptide. In some preferred embodiments, the peptide is a constrained peptide. In some embodiments, the peptide comprises

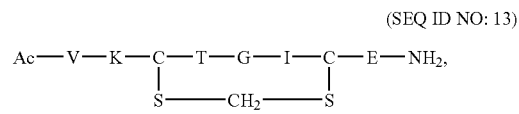

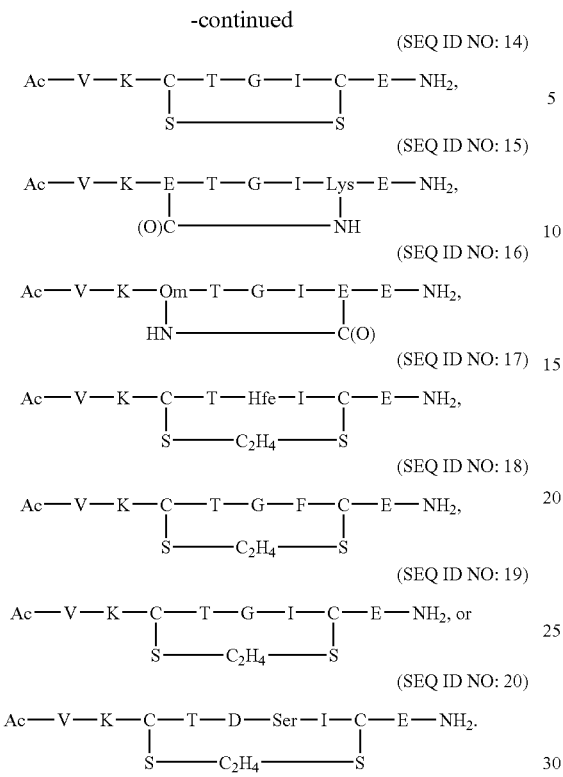

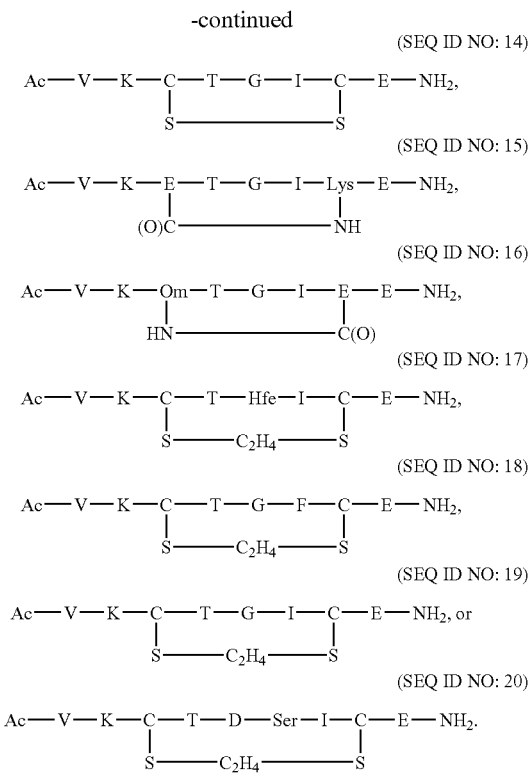

In some embodiments, the GTPγS is present at a concentration of between 0.2 nM and 50nM. In some embodiments, the method further provides GTP and GDP. In some embodiments, the GTP is present at a concentration of between 100 nM and 10 μM, and preferably, at a concentration of between 990 nM and 2 μM. In some embodiments, the GDP is present at a concentration of between 100 nM and 10 μM, and preferably, at a concentration of between 990 nM and 2 μM, and even more preferably, at a concentration of 1 μM. In some embodiments, the G protein coupled receptor is present at a concentration of at least 10 pmoles/mg, and preferably, at a concentration of at least 20 pmol/mg.

In still further embodiments, the present invention provides a method, comprising providing a peptide that inhibits the GTPase acceleration activity of an RGS protein, wherein the peptide binds to said RGS protein; at least one test compound; and contacting the test compound and the peptide under conditions such that the ability of the test compound to inhibit the binding of the peptide to the RGS protein is determined. In some embodiments, the RGS protein is selected from the group including, but not limited to, $G_i$ coupled RGS proteins, $G_s$ coupled RGS proteins, $G_q$ coupled RGS proteins, $G_{12/13}$ coupled RGS proteins and $G_o$ coupled RGS proteins. For example, in some embodiments, the RGS protein is selected from the group including, but not limited to, RGS4 and RGS8. In some embodiments, the peptide is a constrained peptide. For example, in some embodiments, the peptide comprises

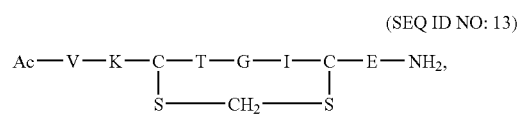

In some embodiments, the test compound is a peptide mimetic. In some embodiments, the test compound is a drug. The present invention additionally provides a drug identified by the method disicosed herein.

In yet other embodiments, the present invention provides a method, comprising providing a Gα protein; a GTPγS-fluorophore; at least one RGS protein; and at least one test compound; and incubating the Gα protein with the GTPγS-fluorophore, the test compound, and the at least one RGS protein, under conditions such that the fluorophore emits a fluorescent signal, wherein the fluorescent signal is stabilized by the RGS protein; determining the level of the fluorescent signal over time relative to the level in the absence of said test compound. In some embodiments, the Gα is Gα$_o$. In some embodiments, the fluorophore is BODIPY. In some embodiments, the RGS protein comprises RGS4 or RGS8. In some embodiments, the test compound is a peptide. In some embodiments, the peptide is a constrained peptide. In some embodiments, the peptide comprises

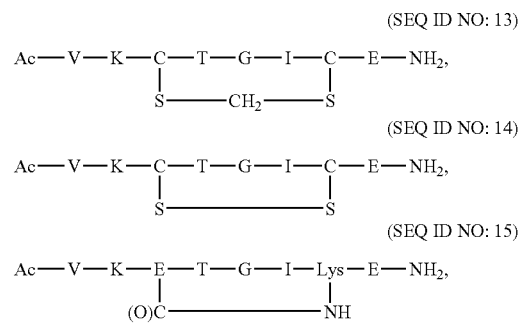

-continued

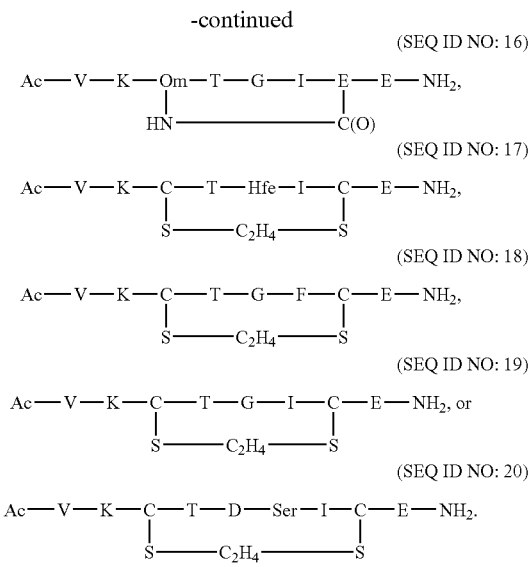

(SEQ ID NO: 16)
(SEQ ID NO: 17)
(SEQ ID NO: 18)
(SEQ ID NO: 19)
(SEQ ID NO: 20)

In some embodiments, the test compound is a peptide mimetic. In some embodiments, the test compound is a drug. In other embodiments, the present invention provides a drug identified by the described method.

DESCRIPTION OF THE FIGURES

FIG. 1 shows a Table describing various RGS proteins and their functional effects (Zhong and Neubig, Journal of Phaimacol. and Exp. Ther., 297:837 [2001]).

FIG. 2 illustrates the crystal structure of RGS4 and $G\alpha_{i1}$.

FIG. 5 shows a model of the Receptor-G Protein cycle without (FIG. 5A) and with (FIG. 5B) RGS.

FIG. 10A illustrates the inhibitory activity of the YJ14 peptide. FIG. 10B illustrates the inhibitory activity of the YJ13 peptide. FIG. 10C illustrates the inhibitory activity of the YJ16 peptide. FIG. 10D shows a table summarizing the inhibitory data of FIGS. 10A-C.

FIG. 12 shows a Table of RGS proteins involved in CNS function.

FIG. 13 shows a Table of receptor-specific actions of RGS proteins.

DEFINITIONS

To facilitate understanding of the invention, a number of terms are defined below.

As used herein, the term "host cell" refers to any cell (e.g., eukaryotic cells such as mammalian cells, avian cells, amphibian cells, plant cells, fish cells, and insect cells or prokaryotic cells such as bacteria or virus), whether located in vitro or in vivo.

As used herein, the term "inhibits the GTPase acceleration activity-of an RGS protein" refers to a conditions (e.g., the addition of an inhibitor of the present invention) that reduces the GTPase acceleration activity of the RGS protein by at least about 15 percent, preferably by at least 50 percent, more preferably by at least 90 percent, and most preferably at least 99 percent. The GTPase acceleration activity can be measured using any suitable method including, but not limited to, the methods described in Examples 1 and 2 below.

As used herein, the term "GTPase acceleration activity" as in the GTPase acceleration activity of an RGS protein refers to an acceleration of GTP hydrolysis in the presence of RGS protein relative to the absence.

As used herein, term "determining the amount of said GTPγS bound to said Gprotein" refers to the quantitative or semi-quantitative measurement of the amount GTPγS bound to a G-protein in the presence of a G protein receptor. The amount may be measured using any suitable assay including, but not limited to, the assays described in Examples 1 and 2.

As used herein, the term "contacting said test compound and said peptide under conditions such that the ability of said test compound to inhibit the binding of said peptide to said RGS protein is determined" refers to the measurement of the ability of test compounds to compete for binding to RGS protein in the presence of an peptide inhibitor of the present invention. The binding may be determined using any suitable method. For example, in some embodiments, binding is determined by labeling the peptide inhibitor and determining the amount of peptide inhbitor bound in the presence and absence of the test compound.

Figure 2A:
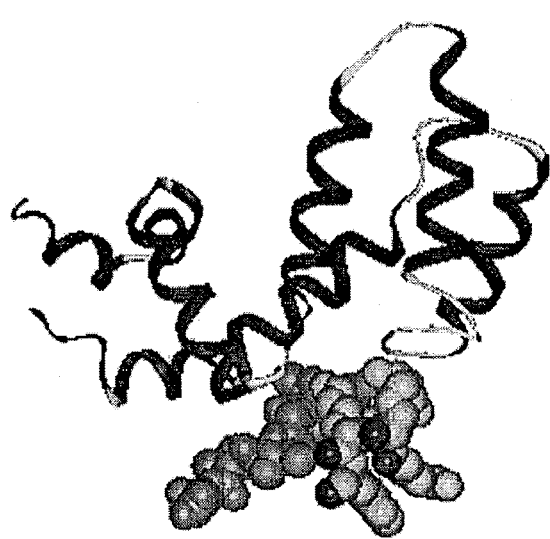
FIG. 2A illustrates the RGS protein (ribbon) and the major $G\alpha$ contact sites (switch I and switch II). The switch I peptide includes residues 180-186 (KTTGIVE; SEQ ID NO:1).
Figure 2B:
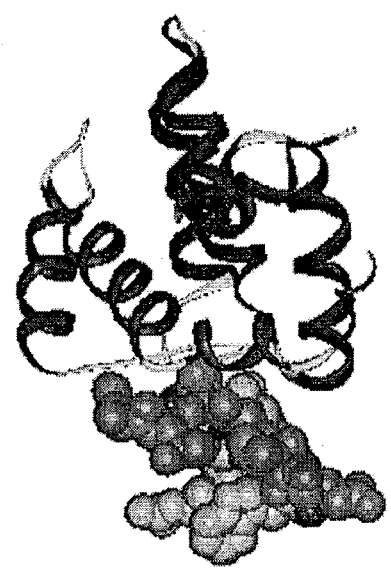
FIG. 2B illustrates the bend in the $G\alpha$ switch I peptide which extends threonine 182 into the RGS-$G\alpha$ binding pocket. Residues T181 and V185 point away from the RGS surface and were modified to introduce conformational constraints.

As used herein, the term "mimetic" refers to a small molecule compound that mimics the binding of a ligand to its target. For example, a mimetic of a peptide inhibitor of an RGS protein is a small molecule that binds to the same site of the RGS protein as does the peptide (See e.g., FIG. 2). In some preferred embodiments, mimetic compounds are those in which the peptide cycle is replaced by any non-peptide scaffold that allows comparable positioning of functional equivalents of the K, T, and E sidechains of the peptide inhibitors of the present invention.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "genome" refers to the genetic material (e.g., chromosomes) of an organism.

As used herein, the term "signal protein" refers to a protein that is co-expressed with a protein of interest and which, when detected by a suitable assay, provides indirect evidence of expression of the protein of interest. Examples of signal proteins include, but are not limited to, immunoglobulin heavy and light chains, beta-galactosidase, beta-lactamase, green fluorescent protein, and luciferase.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length protein or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "constrained peptide" refers to any peptide chain comprising at least one non-peptide bond between two or more amino acids. The nonpeptide bond is in addition to any peptide bonds in-between each amino acid in the peptide. In some embodiments, the non-peptide bond is between two non-contiguous amino acids. In other embodiments, the non-peptide bond is between adjacent amino acids. Constrained peptides may also include additional atoms or molecules as part of the non-peptide bond. Exemplary constrained peptides include, but are not limited to, those described in Table 2.

As used herein, the term "GTPγS-fluorophore" refers to a GTPγS that has a physical interaction with a fluorophore. In some embodiments, the interaction is covalent. For example, in some embodiments, the fluorophore is covalently attached to the S atom. In preferred embodiments, the fluorescense signal from the GTPγS-fluorophore is stabilized by the presence of a RGS protein and Gα subunit.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthineguanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk⁻ cell lines, the CAD gene which is used in conjunction with CAD-deficient cells and the mammalian hypoxanthine-guanine phosphoribosyl transferase (hprt) gene which is used in conjunction with hprt⁻ cell lines. A review of the use of selectable markers in mammalian cell lines is provided in Sambrook, J. et al., *Molecular Cloning: A Laboratory Manual*, 2nd ed., Cold Spring Harbor Laboratory Press, New York (1989) pp. 16.9-16.15.

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

As used herein, the term "response," when used in reference to an assay, refers to the generation of a detectable signal (e.g., accumulation of reporter protein, increase in ion concentration, accumulation of a detectable chemical product).

As used herein, the term "membrane receptor proteins" refers to membrane spanning proteins that bind a ligand (e.g., a hormone or neurotransmitter). As is known in the art, protein phosphorylation is a common regulatory mechanism used by cells to selectively modify proteins carrying regulatory signals from outside the cell to the nucleus. The proteins that execute these biochemical modifications are a group of enzymes known as protein kinases. They may further be defined by the substrate residue that they target for phosphorylation. One group of protein kinases is the tyrosine kinases (TKs), which selectively phosphorylate a target protein on its tyrosine residues. Some tyrosine kinases are membrane-bound receptors (RTKs), and, upon activation by a ligand, can autophosphorylate as well as modify substrates. The initiation of sequential phosphorylation by ligand stimulation is a paradigm that underlies the action of such effectors as, for example, epidermal growth factor (EGF), insulin, platelet-derived growth factor (PDGF), and fibroblast growth factor (FGF). The receptors for these ligands are tyrosine kinases and provide the interface between the binding of a ligand (hormone, growth factor) to a target cell and the transmission of a signal into the cell by the activation of one or more biochemical pathways. Ligand binding to a receptor tyrosine kinase activates its intrinsic enzymatic activity (See, e.g., Ullrich and Schlessinger, Cell 61:203-212 [1990]). Tyrosine kinases can also be cytoplasmic, non-receptor-type enzymes and act as a downstream component of a signal transduction pathway.

As used herein, the term "signal transduction protein" refers to proteins that are activated or otherwise affected by ligand binding to a membrane receptor protein or some other stimulus. Examples of signal transduction protein include adenyl cyclase, phospholipase C, and G-proteins. Many membrane receptor proteins are coupled to G-proteins (i.e., G-protein coupled receptors (GPCRs); for a review, see Neer, 1995, Cell 80:249-257 [1995]). Typically, GPCRs contain seven transmembrane domains. Putative GPCRs can be identified on the basis of sequence homology to known GPCRs.

GPCRs mediate signal transduction across a cell membrane upon the binding of a ligand to a GPCR (e.g., to the extracellular portion). The intracellular portion of a GPCR interacts with a G-protein to modulate signal transduction from outside to inside a cell. A GPCR is therefore said to be "coupled" to a G-protein. G-proteins are composed of three polypeptide subunits: an α subunit, which binds and hydrolyses GTP, and a dimeric βγ subunit. In the basal, inactive state, the G-protein exists as a heterotrimer of the α and βΓ sub-units. When the G-protein is inactive, guanosine diphosphate (GDP) is associated with the α subunit of the G-protein. When a GPCR is bound and activated by a ligand, the GPCR binds to the G-protein heterotrimer and decreases the affinity of the Gα subunit for GDP. In its active state, the G subunit exchanges GDP for guanosine triphosphate (GTP) and active Gα subunit disassociates from both the receptor and the dimeric βγ subunit. The disassociated, active Gα or βγ subunits transduce signals to effectors that are "downstream" in the G-protein signaling pathway within the cell. Eventually, the G-protein's endogenous GTPase activity returns Gα subunit to its inactive state, in which it is associated with GDP and the dimeric βγ subunit.

Numerous members of the heterotrimeric G-protein family have been cloned, including more than 20 genes encoding various Gα subunits. The various G subunits have been categorized into four families, on the basis of amino acid sequences and functional homology. These four families are termed $G\alpha_s$, $G\alpha_s$, $G\alpha_q$, and $G\alpha_{12}$. Functionally, these four families differ with respect to the intracellular signaling pathways that they activate and the GPCR to which they couple.

For example, certain GPCRs normally couple with $G\alpha_s$ and, through $G\alpha_s$, these GPCRs stimulate adenylyl cyclase activity. Other GPCRs normally couple with $G\alpha_q$, and through $G\alpha_q$, these GPCRs can activate phospholipase C (PLC), such as the β isoform of phospholipase C (i.e., PLCβ, Sternweis and Smrcka, Trends in Biochem. Sci. 17:502506 [1992]).

As used herein, the term "$G_i$ coupled RGS protein" refers to a RGS protein that modulates the activity of a $G_i$ protein. As used herein, the term "Go coupled RGS protein" refers to a RGS protein that modulates the activity of a Go protein.

As used herein, the term "a peptide that inhibits the GTPase acceleration activity of a RGS protein" refers to a peptide that decreases the GTPase acceleration activity of an RGS protein by inhibiting the ability of the RGS protein to interact with G proteins. In some embodiments, the peptides bind to the RGS proteins. In some preferred embodiments, the peptides are the peptides disclosed herein.

As used herein, the term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250-300 amino acid catalytic domain. This domain can be further divided into 11 subdomains. N-terminal subdomains I-IV fold into a two-lobed structure that binds and orients the ATP donor molecule, and subdomain V spans the two lobes. C-terminal subdomains VI-XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII, which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity (See, e.g., Carbonneau, H. and Tonks, Annu. Rev. Cell Biol. 8:463-93 [1992]). Regulation of PTK activity may therefore be an important strategy in controlling some types of cancer.

Examples of protein kinases include, but are not limited to, cAMP-dependent protein kinase, protein kinase C, and cyclin-dependent protein kinases (See, e.g., U.S. Pat. Nos. 6,034,228; 6,030,822; 6,030,788; 6,020,306; 6,013,455; 6,013,464; and 6,015,807, all of which are incorporated herein by reference).

As used herein, the term "protein phosphatase" refers to proteins that remove a phosphate group from a protein. Protein phosphatases are generally divided into two groups, receptor and non-receptor type proteins. Most receptor-type protein tyrosine phosphatases contain two conserved catalytic domains, each of which encompasses a segment of 240 amino acid residues (See e.g., Saito et al., Cell Growth and Diff. 2:59 [1991]). Receptor protein tyrosine phosphatases can be subclassified further based upon the amino acid sequence diversity of their extracellular domains (See e.g., Krueger et al., Proc. Natl. Acad. Sci. USA 89:7417-7421 [1992]). Examples of protein phosphatases include, but are not limited to, cdc25 a, b, and c, PTP20, PTP1D, and PTPλ (See e.g., U.S. Pat. Nos. 5,976,853; 5,994,074; 6,004,791; 5,981,251; 5,976,852; 5,958,719; 5,955,592; and 5,952,212, all of which are incorporated herein by reference).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, μ-galactosidase, alkaline phosphatase, and horse radish peroxidase.

As used herein, the term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_M$" as used herein refers to the Michaelis-Menton constant for an enzyme and is defined as the concentration of the specific substrate at which a given enzyme yields one-half its maximum velocity in an enzyme catalyzed reaction.

The term "test compound" refers to any chemical entity, pharmnaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

The present invention relates to novel inhibitors of regulators of G-protein signaling and methods of screening for such inhibitors. In particular, the present invention provides peptide inhibitors of regulator of G-protein signaling (RGS) proteins and methods of using such inhibitors to modulate physiological effects of G protein and receptor signaling. The present invention also provides assays for use in the screening of candidate RGS protein inhibitors.

I. RGS Inhibitors

In some embodiments, the present invention provides inhibitors of RGS protein mediated acceleration of G protein GTPase activity and/or RGS protein binding to G protein. In some embodiments, the inhibitors are peptides. In some preferred embodiments, the peptides are constrained.

A. RGS Proteins

Figure 14:
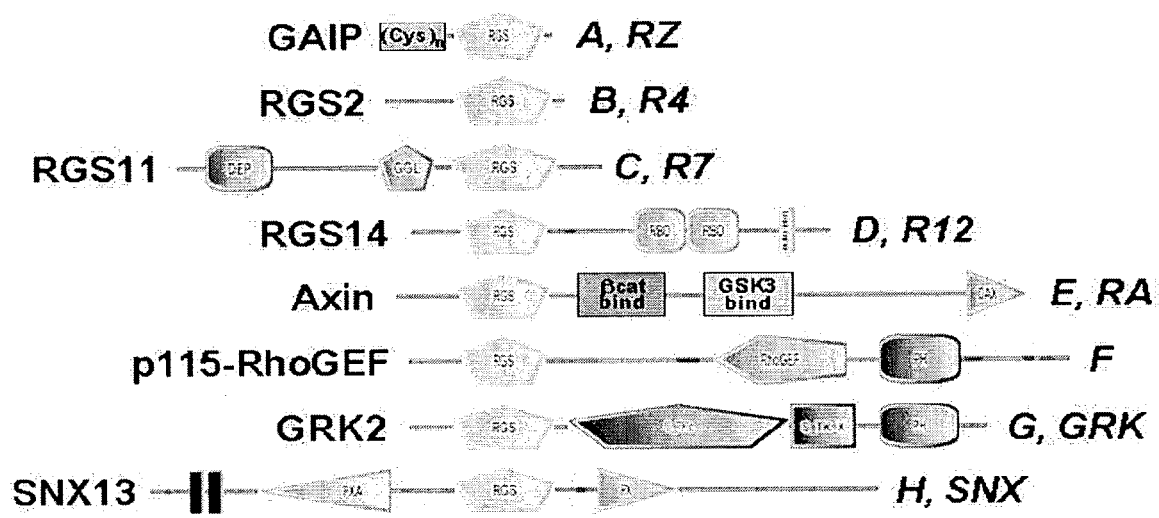
FIG. 14 shows representative members of the eight RGS protein subfamilies.

RGS protein are a highly diverse protein family, which have unique tissue distributions and functions. RGS proteins can be divided into 8 subfamilies (See FIG. 14) and share a conserved "RGS box" domain (DeVries et al., Proc Natl Acad Sci USA 92: 11916 [1995]). FIGS. 1, 12, and 13 show Tables of various RGS proteins, their tissue distribution, target G proteins, and proposed functions.

The present invention is not limited to the inhibition of a particular RGS protein. RGS proteins are classified by the type of G protein that they interact with (e.g., including, but not limited to, $G_i$, $G_o$, $G_q$, $G_t$, $G_s$, $G_z$, and $G_{12/13}$ coupled RGS proteins). Alternatively, RGS proteins are classified based on sub family (See e.g., FIG. 12; Zheng et al., Trends Biochem. Sci., 24:411 [1999]). The present invention contemplates inhibitors of any number of RGS proteins including, but not limited to, those disclosed herein.

The present invention is not limited to a particular mechanism. Indeed, an understanding of the mechanism is not necessary to practice the present invention. Nonetheless, it is contemplated that RGS proteins represent novel pharmacological/therapeutic targets. Drugs targeting RGS proteins include, but are not limited to: 1) potentiators of endogenous agonist function, 2) potentiators/desensitization blockers of exogenous GPCR agonists, 3) specificity enhancers of exogenous agonists, 4) antagonists of effector signaling by an RGS protein, and 5) RGS agonists (See e.g., Zhong and Neubig, Journal of Pharmacol. and Exp. Ther., 297:837 [2001]). It is contemplated that inhibitors of the present invention inhibit both the GTPase acceleration activity of RGS proteins, as well as the binding of RGS proteins to G proteins. For example, the F family (e.g. p115rhoGEF) of RGS proteins mediate signaling via RGS binding to Gα, which leads to activation of the rhoGEF activity of the RGS protein. Thus, it is contemplated that inhibition of Galpha-13 binding to the RGS domain of p115rhoGEF blocks Rho activation, which is contemplated to be involved in metastasis (See e.g., Nature, 2000 August 3;406(6795): 532-5.)

For example, it is contemplated that that RGS inhibitors of the present invention find use in the treatment of Alzheimer's disease, depression, epilepsy, Parkinson's disease, pain, and spasticity.

It is further contemplated that RGS proteins are involved in the modulation, diagnosis, and treatment of immune disorders, additional psychiatric disorders, cardiovascular disease, respiratory disorders, and cancer metastasis (See e.g., U.S. Pat. Nos. 6,274,362, 6,069,296, and 5,929,207; each of which is herein incorporated by reference). Thus, RGS proteins provide new opportunities for drug development.

B. Inhibitors of RGS Proteins

In some embodiments, the present invention provides a series of compounds that show inhibitory activity towards a variety of RGS proteins. The specificity for different RGS proteins and structure-activity relations for the series of compounds is described in Example 3 below. In preferred embodiments, inhibitors of RGS function by binding to the site on the RGS protein at which the G protein alpha subunit binds. Based on the crystal structure of the Gα$_{i1}$ RGS4 complex (Coleman and Sprang, J. Biol. Chem. 274:16669 [1999]), there are two major regions of contact of RGS on the Gα subunit (Switch I and Switch II). During the course of development of the present invention, peptide inhibitors were prepared based on the Switch I sequence of the Gα subunit and tested for their ability to inhibit RGS activity. The initial linear peptides were found to be inactive. Examination of the crystal structure revealed a novel bend in the Gα subunit in the Switch I region. The present invention is not limited to a particular mechanism. Indeed, an understanding of the mechanism is not necessary to practice the present invention. Nonetheless, it is contemplated that constrained peptides effectively mimic the conformation of the Switch I region. Thus, a series of constrained peptides in which the linear sequence was internally cyclized were made and found to have significant activity.

A series of peptides that bind to RGS4, RGS7, and RGS8 for use as RGS inhibitors or in the design of RGS inhibitors was generated from the Switch I sequence of Gα$_{i1}$. The peptides were designed to bind to the RGS protein at the same site as does the Gα subunit, which is the biochemical target of the RGS proteins. The present invention thus provides useful inhibitors of RGS binding to and action on Gα as well as defining a contact site between the RGS proteins and the Gα subunit.

The present invention is not limited to a particular mechanism. Indeed, an understanding of the mechanism is not necessary to practice the present invention. Nonetheless, it is contemplated that the site with which the peptide interacts finds use as a novel target for drug action. Accordingly, additional uses of the compounds of the present invention include, but are not limited to: 1) development of pro-drugs which deliver the peptide to intracellular sites (e.g., by masking charged groups with cleavable lipophilic moieties to pass the cell membrane), 2) using the structure-activity relations defined herein to design peptido-mimetic or small molecule RGS inhibitors, and 3) obtaining crystal structures of the complex of the peptide and RGS protein to specify a well-defined site for small molecule inhibitor design. The present invention is not limited to the particular peptide inhibitors disclosed herein. Indeed, it is contemplated that peptide inhibitors can be designed for a variety of RGS proteins (e.g., from additional families and coupled to additional G proteins). For example, it is contemplated that a peptide that bound to Gs RGSs would inhibit Family H RGSs e.g., SNX13, peptides that bound to G12 or G13 RGSs would inhibit Family F RGSs e.g., p115rhoGEF, and Gq peptides would inhibit Family G RGSs, e.g., GRK2).

Thus, it is contemplated that the general structural motif of

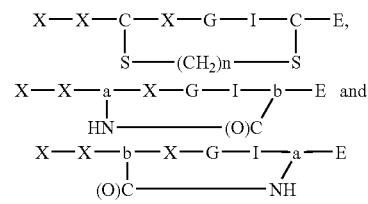

respectively, SEQ ID NOS: 10, 11, and 12, can be substituted with specific sequences compatible with a particular RGS (See e.g., Table 1 below). In preferred embodiments, the residue indicated by a consists of an amino acid with an amine in the side chain (e.g, lysine, A$_2$bu, ornithine, etc.) and b consists of an amino acid having a carboxyl group in the side chain (e.g., aspartate, glutamate, etc).

TABLE 1

Gα Subunit Switch 1 Sequences for RGS Inhibitor Design

| | G protein | Sequences[2,3,4] | RGS family | RGS proteins |
|---|---|---|---|---|
| RGS4-inhibitor[1] G protein Family | | VKCTGICE (SEQ ID NO: 21) | | |
| Gi | i1, i2, i3, o | VKTTGIVE (SEQ ID NO: 2) | A B C D | 3456789 etc. |
| Gi | t, g | VKTTGIIE (SEQ ID NO: 3) | A B C | 9 etc. |
| Gi | z | DMTTGIVE (SEQ ID NO: 4) | A | |
| Gq | q, 11, 14 | VPTTGIIE (SEQ ID NO: 5) | A B G | 2345 GRK2 |
| Gq | 15 | MPTTGINE (SEQ ID NO: 6) | Unknown | Unknown |
| G12 | 12 | KATKGIVE (SEQ ID NO: 7) | F | RhoGEF, LARG |
| G12 | 13 | RPTKGIHE (SEQ ID NO: 8) | F | RhoGEF, LARG |
| Gs | s, olf | VLTSGIFE (SEQ ID NO: 9) | H | SNX |

Notes:
[1]This shows the amino acid sequence of the YJ series of RGS inhibitors with cross-links at the underlined positions (3 and 7) with disulfide, thioether, or lactam linkages.
[2]The consensus among all Galpha subunits over this region is XXTXGIXE (SEQ ID NO: 22) so with cross-linking residues in positions 3 and 7, it is possible to vary positions 1, 2, and 4 to obtain specificity for RGS proteins that recognize the different G protein families while keeping the C—C or other bridging chemistry at positions 3 and 7. Thus it is contemplated that any peptide XXCXGICE (SEQ ID NO: 23) with appropriate bridging chemistry would be an appropriate extension of this technology to produce inhibitors of RGS proteins from other families such as family F, G, H. Note: Family E (axin) RGS proteins have not yet been shown to interact with G proteins but should a G protein interaction be identified, a similar approach to inhibitor design could be employed.
[3]Note that among the families, Gz diverges from the other Gi's, G12 and 13 are significantly different, and G15 differs from other Gq's (but in this latter case only at position 7 which is not available for modification due to the cross-link).
[4]The residue in the Ga sequences preceding this octapeptide is R for all G proteins however the residues after the octapeptide vary.

The RGS proteins that interact with the different Gα subunits are indicated in the last two columns.

C. Protease Resistant Peptides

In some embodiments, the peptide inhibitors of the present invention are protease resistant. In one embodiment, such protease-resistant peptides are peptides comprising protecting groups. In a preferred embodiment, the present invention contemplates a peptide of the present invention or variant thereof that is protected from exoproteinase degradation by N-terminal acetylation ("Ac") and C-terminal amidation. Such peptides are useful for in vivo administration because of their resistance to proteolysis.

In another embodiment, the present invention also contemplates peptides protected from endoprotease degradation by the substitution of L-amino acids in said peptides with their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention these mirror-image structures are called the D and L forms of the amino acid. These forms cannot be interconverted without breaking a chemical bond. With rare exceptions, only the L forms of amino acids are found in naturally occurring proteins.

D. Mimetics

In still further embodiments, the present invention contemplates compounds mimicking the necessary conformation for recognition and docking to the receptor binding to the peptides of the present invention are contemplated as inhibitors of RGS proteins. A variety of designs for such mimetics are possible. For example, cyclic-containing peptides, in which the necessary conformation for binding is stabilized by nonpeptides, are specifically contemplated. U.S. Pat. No. 5,192,746, U.S. Pat. No. 5,169,862, U.S. Pat. No. 5,539,085, U.S. Pat. No. 5,576,423, U.S. Pat. No. 5,051,448, and U.S. Pat. No. 5,559,103, all hereby incorporated by reference, describe multiple methods for creating such compounds.

Synthesis of nonpeptide compounds that mimic peptide sequences is also known in the art. Eldred et al. (J. Med. Chem., 37:3882 [1994]) describe nonpeptide antagonists that mimic the Arg-Gly-Asp sequence. Likewise, Ku et al. (J. Med. Chem., 38:9 [1995]) give further elucidation of the synthesis of a series of such compounds. Such nonpeptide compounds that mimic peptide inhibitors of the present invention are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexycarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the peptides described herein (including, but not limited to, peptides in which L-amino acids are replaced by their D-isomers). One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, Proc. Natl. Acad. Sci. (USA), 85:2444-2448 (1988); Lipman and Pearson, Science, 227:1435 (1985)). In the present invention, synthetic polypeptides useful in inhibiting RGS proteins are those peptides with statistically significant sequence homology and similarity (Z value of Lipman and Pearson algorithm in Monte Carlo analysis exceeding 6).

In some particularly preferred embodiments, mimetic compounds are those in which the peptide cycle is replaced by any non-peptide scaffold that allows comparable positioning of functional equivalents of the K, T, and E sidechains of the peptide inhibitors.

E. Other Modified Peptides

The present invention further includes peptides modified to improve one or more properties useful in pharmaceutical compounds. For example, in some embodiments, peptides are modified to enhance their ability to enter intracellular space. Such modifications include, but are not limited to, the addition of charged groups, lipids and myristate groups (See e.g., U.S. Pat. No. 5,607,691; herein incorporated by reference).

In other embodiments, the peptides of the present invention may be in the form of a liposome in which isolated peptide is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

II. Drug Screening Methods

In some embodiments, the present invention provides methods of identifying potential drug targets of RGS proteins (e.g., the peptides described above). For example, in some embodiments, the present invention provides drug-screening methods utilizing G protein subunits, G protein receptors, and RGS proteins. In still further embodiments, the present invention provides a fluorescence based drug screening method utilizing G protein receptors, RGS proteins, and labeled GTP derivatives.

A. CHO Membrane Assays

In some embodiments, the present invention provides methods of assaying for inhibitors of RGS proteins utilizing membranes comprising G protein subunits.

1. GTPase Assays

In some embodiments, the membrane assay comprises a GTPase assay (See e.g, Berman et al., J. Biol. Chem., 271:

27209 [1996] and Berman et al., Cell 86:445 [1996]). In such embodiments, $\alpha_{2A}$ adrenergic receptor expressing membranes are pre-incubated with $\gamma$-$^{32}$P GTP and RGS proteins. In some embodiments, membranes contain both $\alpha_{2A}$ adrenergic receptor and $G\alpha_o$ subunits, allowing measurement of both $G_i$ and $G_o$-coupled RGS proteins. In some embodiments, a steady-state GTPase assay is utilized to assay RGS inhibitors (See e.g., Wise and Milligan, J. Biol. Chem., 272:24673 [1997]).

2. GTPγS Binding Assays

In preferred embodiments, a GTPγS Binding Assay is utilized in drug screening applications. The methods of the present invention provide a simple radioligand binding method to assess the function of RGS proteins in the context of specific receptors in mammalian cell membranes (See e.g., Examples 1 and 2). This method does not require the use of the complex charcoal separation or single-turnover kinetic measurements which are used in the standard GTPase method (e.g., the method described above) to assess RGS function, provides an RGS-dependent functional response with excellent signal/noise ratio and is amenable to high-throughput screening methodologies. The method of the present invention measures receptor-stimulated labeled GTPγS binding to cell membranes containing a particular G protein-coupled receptor to assess RGS function. In some embodiments, the label is [$^{35}$S]. In other embodiments, a non-radioactive (e.g., fluorescent or luminescent) label is utilized. It is preferred that several assay parameters are maintained at specific levels that were elucidated during the development of the present invention.

A major advance of this drug screening method of the present invention is the simple application of standard radioligand binding methods to assess the activity of RGS proteins and the inhibition thereof by potential drug candidates. This has been a major obstacle blocking this new field and finds use for application by many drug companies. Every large drug company has a major program in G protein coupled receptor agonists and antagonists. The novel RGS family of proteins modulates the activity of G proteins in a manner distinct from that of receptors. Furthermore, RGS proteins have tissue specific distributions that render them useful as drug targets. Thus, the present invention provides a simple method of assessing RGS protein activity that is amenable to standard high-throughput screening approaches.

B. Fluorescence Assay

In still further embodiments, the present invention provides a fluorescence-based assay for screening RGS inhibitors. The present invention eliminates the need for any separation of components and provides a homogenous fluorescence assay that is amenable to very high throughput methodologies, making it particularly suited to very high throughput screening of large numbers of candidate compounds in the research and pharmaceutical industries.

In some embodiments, the assay utilizes a fluorescent GTP analog (e.g., BODIPY GTPγS) to assess RGS interactions with Gα subunits. The addition of a purified RGS protein to the BODIPY-Gα binding reaction stabilizes the G protein/BODIPY complex enhancing fluorescence at long incubation times (1-2 hr). Experiments conducted during the course of development of the present invention (See e.g., Example 5 and FIGS. 15-18) demonstrated that RGS proteins stabilized the fluorescence signal, as well as that the signal was not inhibited by common perturbants, and was inhibited by an RGS inhibitor of the present invention. The fluorescence enhancement by the RGS protein is very robust (stable from 60 minutes to many hours of incubation).

Experiments conducted during the course of the development of the present invention demonstrated that preferred experimental conditions include a long time of incubation, appropriate choice of temperature (25° C. is a preferred temperature), use of $G\alpha_o$, which has faster kinetics, and low $G\alpha_o$ and BODIPY concentrations.

The present invention is not limited to a particular mechanism. Indeed, an understanding of the mechanism is not necessary to practice the present invention. Nonetheless, it is contemplated that the basis of the fluorescence based method of the present invention is that RGS protein binding to Gα subunits is dependent on the activation state of the G protein with the strongest binding occurring to the active (GTPγS bound) or transition (GDP-AlF4-bound) state conformations of the Gα subunit. BODIPY-GTPγS binds tightly to $G\alpha_o$ (6 nM Kd) but its binding is significantly weaker than that of the parent non-fluorescent GTPγS (which binds with pM affinity). At low concentrations of BODIPY, the Gα subunit is not fully saturated and the Gα subunit becomes inactivated. This leads to a biphasic kinetic curve for BODIPY fluorescence in the presence of $G\alpha_o$ (FIG. 1).

The fluorescent assay of the present invention is not limited to a particular fluorescent GTPγS derivative. Preferred fluorophores are those that exhibit stable fluorescence when bound to a Gα subunit. Particularly preferred fluorophores are those whose fluorescent signal is stabilized by RGS proteins and is not inhibited by common perturbants (e.g., high ionic strength, glycerol, DMSO). The present invention is also not limited to the use of a fluorescent label. In still further embodiments, the method of the present invention utilizes other probes for nucleotide binding and stabilization of assay signal such as low concentrations of [$^{35}$S] GTPγS, mant-GTPγS, etc.

The present invention is also not limited to a particular Gα subunit or RGS protein. The present invention is not limited to a particular mechanism. Indeed, an understanding of the mechanism is not necessary to practice the present invention. Nonetheless, it is contemplated that, since $G\alpha_s$ and $G\alpha_q$ have both been shown to lose activity when subsaturating nucleotide concentrations are used in binding assays, that RGS-mediated stabilization is likely to occur. It is further contemplated that other RGS proteins have similar effects including RGS2 for $G\alpha_q$ and the SNX proteins (RGS-PX1) for $G\alpha_s$, etc.

In yet other embodiments, other experimental methods utilize the RGS-mediated stabilization of G proteins. For example, in some embodiments, this approach uses radiolabeled nucleotide ligands, and other detection methodologies such as fluorescence polarization (which would not be as affected by quenching by colored compounds), etc.

C. Additional Drug Screening Methods

The present invention is not limited to the screening assays described above. Additional drug screening methods are contemplated including, but not limited to, those disclosed herein. For example, it is contemplated that a chemical that displaces the peptide from binding to the RGS protein would also compete for Gα binding to the RGS protein, resulting in inhibition of RGS function. Thus, blockade of peptide (e.g., YJ13) binding to the RGS also serves as a screen for RGS inhibitors.

In other embodiments, RGS inhibitor peptides (e.g., YJ13, YJ16, etc.) are prepared in fluorescently labeled form (e.g., chemically tagged with fluorescein, BODIPY TMR, or additional labels such as luminescent labels). Since the peptides can be made synthetically, fluorescent tagging can be easily included in the synthesis. The fluorescently tagged forms are then used in high-throughput assays for other drug molecules. Displacement of the fluorescently labeled peptide from the RGS is detected by a number of standard fluorescence methodologies including, but not limited to, fluorescence polarization in a solution phase method and physical release from RGS protein bound to a plate. Other standard fluorescence methods including, but not limited to, dequenching of fluorphore released from the RGS, protection of the bound fluorphore from quenching by external quenching agents, can be used when the properties of the RGS-bound fluorescent peptide are different from the properties of the free peptide.

III. Pharmaceutical Compositions

The present invention further provides pharmaceutical compositions that may comprise peptide inhibitors of RGS signaling, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by abnormal G-protein signaling. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, peptides can be administered to a patient alone, or in combination with drugs or hormones or in pharmaceutical compositions where they are mixed with excipient(s) or other pharmaceutically acceptable carriers. In one embodiment of the present invention, the pharmaceutically acceptable carrier is pharmaceutically inert. In another embodiment of the present invention, peptides may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of RGS inhibitor peptide may be that amount that suppresses abnormal G-protein signaling. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compounds, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For peptide inhibitors of RGS, conditions indicated on the label may include treatment of conditions related to abnormal G protein signaling.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of peptide that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See e.g., U.S. Pat. Nos. 4,657,760; 5,206,344; or 5,225,212, all of which are herein incorporated by reference). Administration to the bone marrow may necessitate delivery in a manner different from intravenous injections.

EXPERIMENTAL

The following examples serve to illustrate certain preferred embodiments and aspects of the present invention and are not to be construed as limiting the scope thereof. In the experimental disclosure which follows, the following abbreviations apply: M (molar); mM (millimolar); µM (micromolar); nM (nanomolar); mol (moles); mmol (millimoles); µtmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade); GTP (guanosine 5'-triphosphate).

Example 1

Method of Assaying RGS-Mediated GTPase Acceleration

This example describes a novel method of assaying for inhibitors of RGS-mediated GTPase Acceleration. A modified version of the [$^{35}$S] GTPγS binding method described in Wieland et al., 1994 (Wieland et al., Methods Enzymol. 237:3 [1994]) was utilized, with the exception that an RGS protein was included to enhance the receptor stimulation of GTPγS binding. RGS-mediated enhancement of receptor-stimulated [$^{35}$S]GTPγS binding was determined in CHO cell membranes expressing high densities (10-20 pmol/mg) of receptor. The method is not limited to the alpha 2a adrenergic receptor or the CHO membrane described herein. The membrane can be from other cell types and/or expressing other G protein coupled receptors (e.g., including, but not limited to, other $G_i$ coupled receptors).

The assay buffer was 50 mM Tris, 5 mM $MgCl_2$, 1 mM EDTA, 100 mM NaCl, 1 mM DTT, pH 7.6. The reaction mixture also contained the following components. Some preferred embodiments include at least one of the components marked with an *.

1. High nanomolar or low micromolar concentrations (typically 1 µM) of GDP.*
2. 4 µg of Chinese hamster ovary (CHO) membranes expressing the alpha 2a adrenergic receptor ($\alpha_{2A}AR$) at a receptor density of ~10-20 pmol/mg. $\alpha_{2A}AR$-CHO membranes were prepared as previously described (Wade et al., Mol. Pharmacol. 56: 1005 [1999]). Membranes were re-suspended in Tris/$MgCl_2$/EGTA (TME) buffer (50 mM Tris, 10 mM $MgCl_2$, 1 mM EGTA, pH 7.6) and were aliquoted before being frozen in liquid $N_2$ and stored at −80° C. until use. The receptor density in the $\alpha_{2a}AR$-CHO membranes was determined by [$^3$H] yohimbine binding and Bradford assay (Bradford, Anal. Biochem. 72: 248 [1976]).
3. 0.2 nM-50 nM [$^{35}$S]GTPγS. A low concentration with respect to the higher concentrations of G protein and GTP utilized is necessary*.
4. Saturating concentration of agonist for the receptor type utilized. UK 14,304 (10 µM).
5. RGS proteins at µM or high nM ranges.
6. GTP at high nM or low µM ranges. This is the most critical component of this method, since the massive GTP hydrolysis accelerated by RGS promotes formation of the empty DRG state which is detected by the low concentration of [$^{35}$S]GTPγS.*

The reaction was started by the addition of either membranes or [$^{35}$S]GTPγS and allowed to proceed for 10 minutes at 30° C. Then, the amount of [$^{35}$S]GTPγS bound is determined. The reactions are stopped by the addition of 3 ml ice-cold washing buffer containing 20 mM Tris, 25 mM $MgCl_2$, 100 mM NaCl, pH 7.7. Samples are rapidly filtered through GF/C filters using a Brandel cell harvester and the bound radioactivity is determined by liquid scintillation counting. Non-receptor-dependent binding is defined by binding in the presence of an antagonist.

Figure 3:
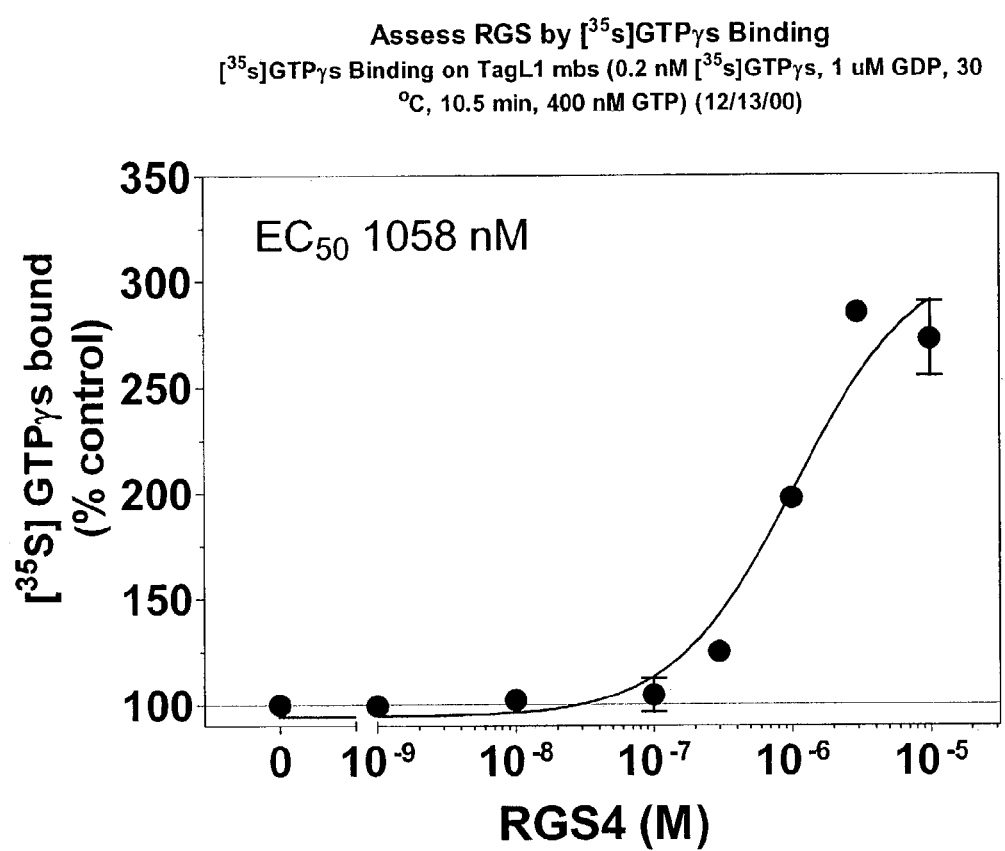
FIG. 3 shows a graph of RGS4 stimulation of [$^{35}$S] GTPγS binding.
Figure 4:
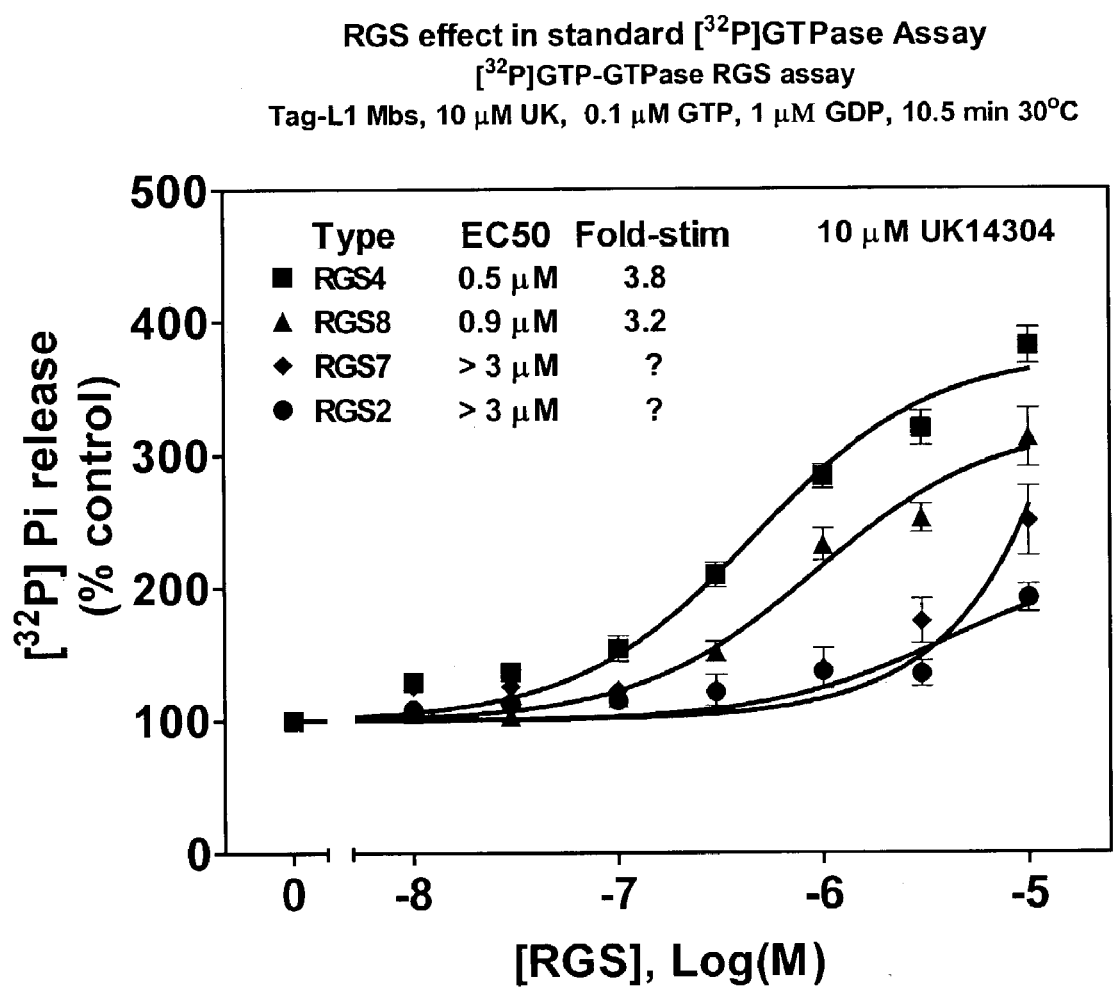
FIG. 4 shows a graph of the effect of RGS in a standard [$^{32}$P] GTPase assay.

This method yields a 3-fold increase in [$^{35}$S] GTPγS binding upon addition of 1 µM RGS4 (FIG. 3). FIG. 4 shows a comparison to the method currently used to assess RGS protein activity with a GTPase assay, which involves [$^{32}$P]GTP, a radioactive compound with a greater radiation hazard and a laborious procedure using a charcoal precipitation step.

Figure 6:
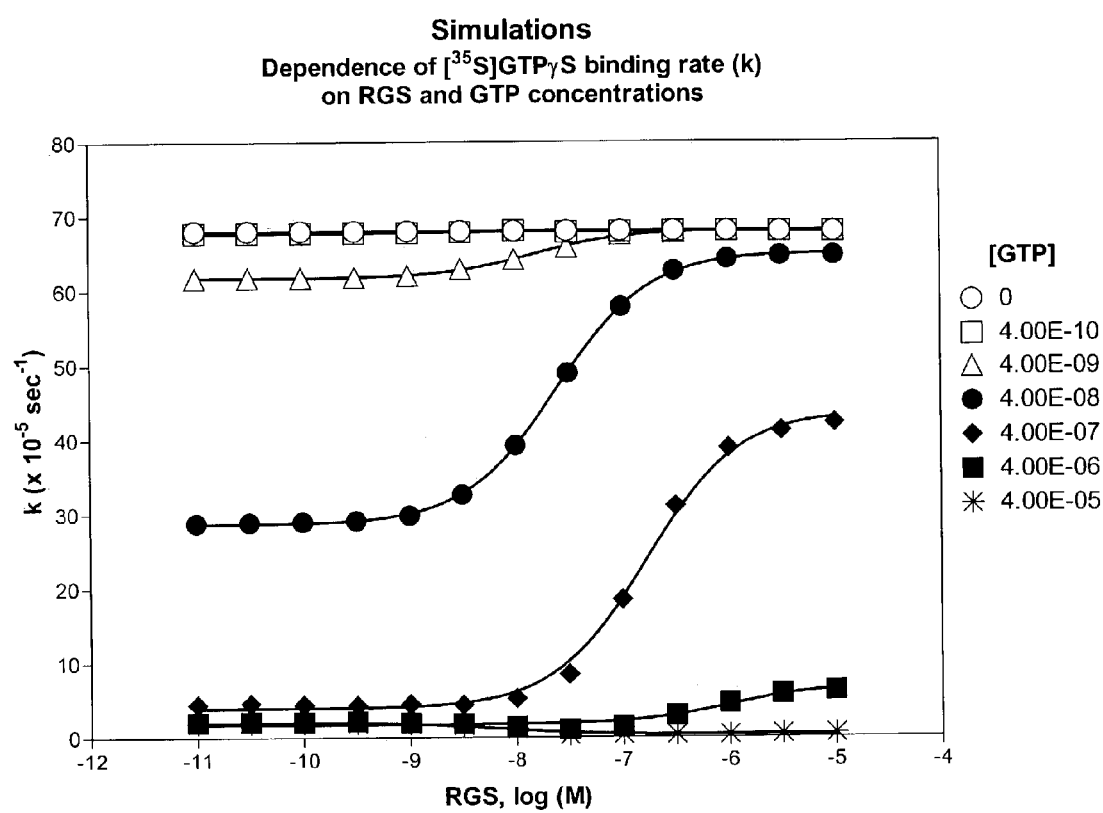
FIG. 6 shows a model of the effect of RGS on receptor-stimulated GTPγS binding. The rate of GTPγS binding to G protein in the presence of agonist and receptor was modeled based on the model parameters in Table 1. With low GTP concentrations the binding of [$^{35}$S] GTPγS is fast but addition of GTP suppresses this rate. At high GTP concentrations (i.e. ≧100-1000 nM) this suppression is reversed by the simulated addition of RGS protein. At low GTP concentrations typically present in GTPγS binding assays (<10 nM, open symbols), there is a minimal effect of RGS on GTPγS binding.

A kinetic model used in the optimization of reaction conditions for the [$^{35}$S] GTPγS binding assay to assess RGS activity is shown in FIG. 5. The model depicts receptor-G protein coupling in the presence of RGS proteins with parameters indicated in Table 2. As can be seen from FIG. 6, the simulations are successful at modeling the mechanism underlying the analysis method.

TABLE 2

Parameters of receptor model including RGS effects

| Step | Function | Forward rate | Backward rate |
|---|---|---|---|
| 1 | Agonist binding to receptor | 1e+6 | 1 |
| 2 | Receptor-G protein coupling | 1e+8 | 1 |
| 3 | Stimulated GDP release | 5 | 1e+6 |
| 4 | GTP binding to DRG | 1e+6 | 0.1 |
| 5 | Dissociation of DRGGTP complex | 2 | 1e+7 |
| 6 | GTP hydrolysis w/o RGS | 0.02 | 0 |
| 7 | Binding of RGS to GGTP | 2e+6 | 2 |
| 8 | GTP hydrolysis with RGS | 30 | 0 |
| 9 | Release of RGS from GGDP | 100 | 1e+5 |

Initial concentration values for components in model

| | |
|---|---|
| D | 1e−5 |
| DR | 0 |
| R | 1e−8 |
| DRGGDP | 0 |
| GGDP | 1e−9 |
| DRG | 0 |
| GDP | 1e−6 |
| DRGGTP | 0 |
| GTP | 4e−7 |
| GGTP | 0 |
| Phos | 0 |
| GGTPRGS | 0 |
| RGS | 1e−6 |
| GGDPRGS | 0 |
| DRGGTPγs | 0 |
| GTPγs | 2e−10 |
| GGTPγs | 0 |

Figure 7:
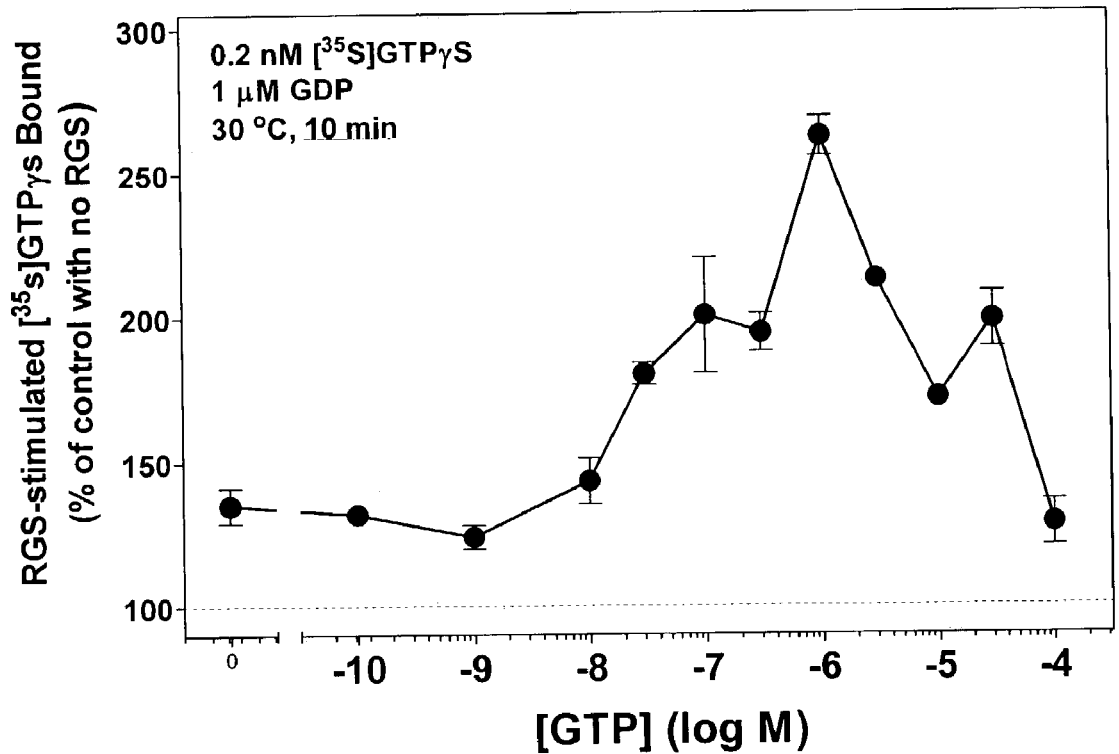
FIG. 7 shows GTP and RGS dependence of $\alpha_{2A}$ adrenergic receptor-stimulated [$^{35}$S] GTPγS binding as an experimental test of the model described in Example 1. The experiment indicates that there is a substantial increase in RGS stimulation of GTPγS binding when 100-3000 nM concentrations of GTP are included in the assay.

Based on the model, it was discovered that high GTP concentrations (~1 μM) are important to obtain a good stimulation of GTPγS binding by the RGS proteins. The present invention is not limited to a particular mechanism. Indeed, an understanding of the mechanism is not necessary to practice the present invention. Nonetheless, it is contemplated that high GTP concentrations are important because at high GTP concentrations, the model is stalled at the GGTP level so that DRG is depleted. When RGS is added, it accelerates GTP hydrolysis (step 8 vs step 6) so that DRG is restored to permit binding of [$^{35}$S] GTPγS. The GTP concentration dependence of [$^{35}$S] GTPγS binding was next investigated (FIG. 7).

Example 2

Addition of Membranes Containing Pertussis Toxin Resistant Gα$_o$ Subunit

Figure 8:
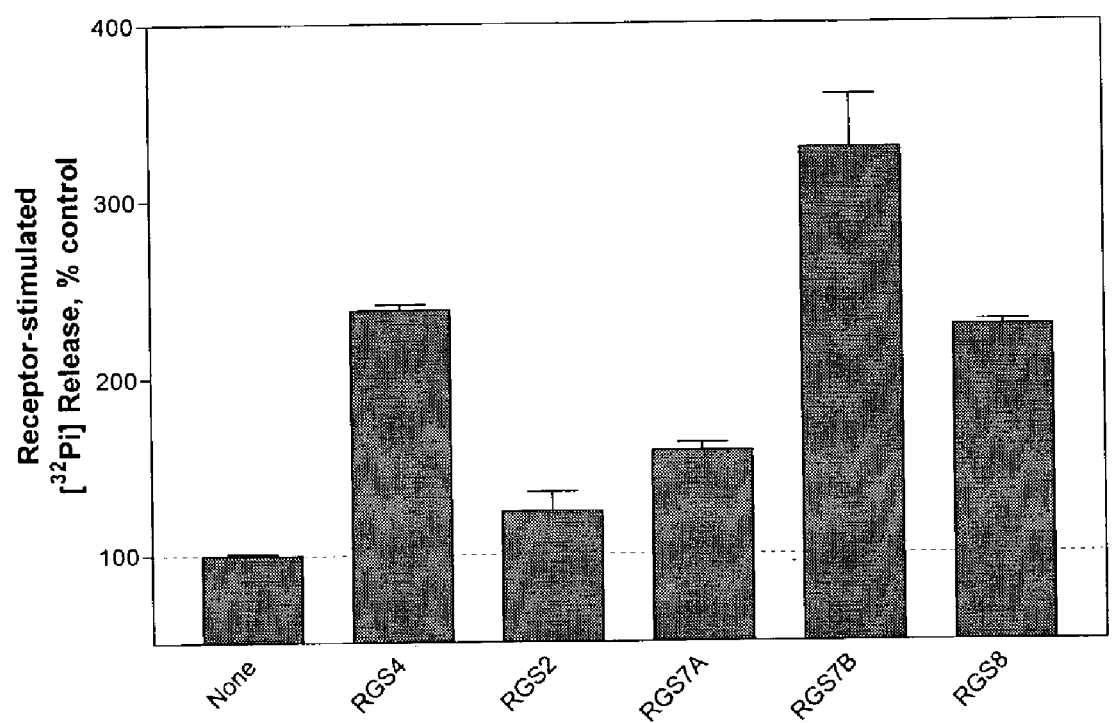
FIG. 8 shows a graph of steady state [$^{32}$P] GTPase activity upon addition of the indicated RGS (1 µM) to $\alpha_{2a}$ Tag-409 cells expressing both the $\alpha_{2a}$ AR and the PTX-resistant $G\alpha_o$ (C351G).
Figure 9:
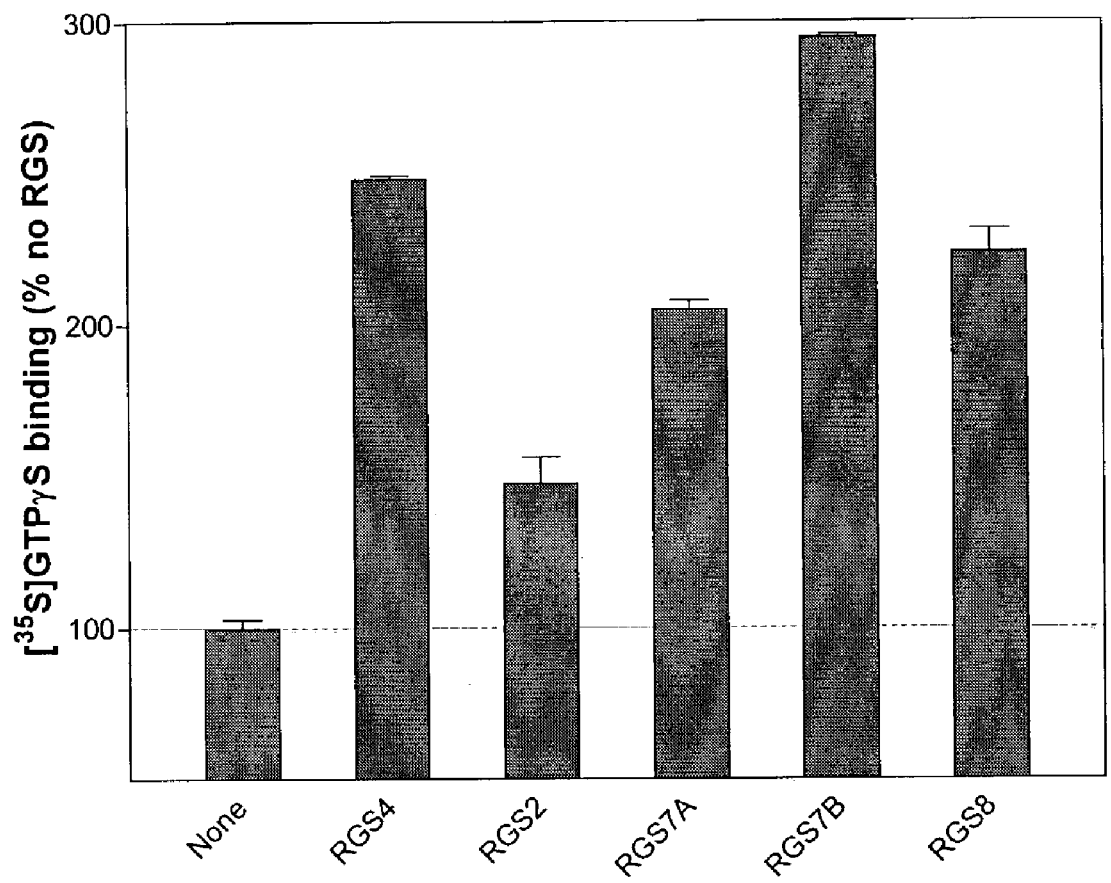
FIG. 9 shows a graph of [$^{35}$S] GTPγS binding activity upon addition of the indicated RGS (1 µM) to $\alpha_{2a}$ Tag-409 cells expressing both the $\alpha_{2a}$ AR and the PTX-resistant $G\alpha_o$ (C351G).

In order to extend the range of RGS proteins for which the membranes described in Example 1 can be used, a pertussis toxin-resistant Gα$_0$ (C351G) subunit was introduced by stable transfection with zeocin selection. These membranes (α$_2$Tag-409) show a strong RGS-mediated GTPase response to both RGS4 and to an RGS7 construct (RGS7B, aa 254-380). This combination of membranes and RGS protein is useful in both the [$^{32}$P] GTPase assay (FIG. 8) and in the [$^{35}$S] GTPγS binding assay (FIG. 9).

Example 3

Inhibition of RGS4-Mediated GTPase Acceleration
　1. Inhibition by VKTTGIVE
　The linear peptide with sequence VKTTGIVE (SEQ ID NO:2) was tested for its ability to inhibit RGS-mediated GTPase acceleration and was found to have no activity.
　2. Inhibition by JMRAc(Et)
　A constrained peptide JMRAc(Et) was found to inhibit RGS-stimulated GTPase activity. Activity was measured by use of CHO cell membranes expressing the α$_{2a}$ AR at high levels (10-20 pmol/mg) described in Example 1 above.
　3. Additional Peptides
　Subsequently, a series of constrained peptides (Table 3) was prepared and the inhibitory activity tested. The inhibitory activity is shown in Table 3 as a relative scale from—(no inhibition) to +++.

| Name | Activity | Peptide Sequence | SEQ ID NO |
|---|---|---|---|
| JO1(Et) | − | V—K—C(—S—C$_2$H$_4$—S)—T—G—I—C—E—NH$_2$ | 24 |
| JMRAc(Et) | +++ | Ac—V—K—C(—S—C$_2$H$_4$—S)—T—G—I—C—E—NH$_2$ | 25 |
| DDH1(Et) | − | V—K—C(—S—C$_2$H$_4$—S)—A$_2$bu—G—I—C—E—NH$_2$ | 26 |
| DDH2(Et) | − | Ac—V—K—C(—S—C$_2$H$_4$—S)—A$_2$bu—G—I—C—E—NH$_2$ | 27 |
| DDH3(Et) | − | V—K—C(—S—C$_2$H$_4$—S)—A$_2$pr—G—I—C—E—NH$_2$ | 28 |

-continued

| Name | Activity | Peptide Sequence | SEQ ID NO |
|---|---|---|---|
| DDH4(Et) | − | Ac—V—K—C(S—C$_2$H$_4$—S)—A$_2$pr—G—I—C—E—NH$_2$ | 29 |
| ES1(Et) | +− | V—K—C(S—C$_2$H$_4$—S)—T—G—F—C—E—NH$_2$ | 30 |
| ES2(Et) | +++ | Ac—V—K—C(S—C$_2$H$_4$—S)—T—G—F—C—E—NH$_2$ | 31 |
| ES3(Et) | − | V—K—C(S—C$_2$H$_4$—S)—T—D—A$_2$bu—I—C—E—NH$_2$ | 32 |
| ES4(Et) | − | Ac—V—K—C(S—C$_2$H$_4$—S)—T—D—A$_2$bu—I—C—E—NH$_2$ | 33 |
| WM1(Et) | ++ | V—K—C(S—C$_2$H$_4$—S)—T—G—Y—C—E—NH$_2$ | 34 |
| WM2(Et) | ++ | Ac—V—K—C(S—C$_2$H$_4$—S)—T—G—Y—C—E—NH$_2$ | 35 |
| YJ1(Et) | +− | V—K—C(S—C$_2$H$_4$—S)—T—D—A$_2$pr—I—C—E—NH$_2$ | 36 |
| YJ2(Et) | ++ | Ac—V—K—C(S—C$_2$H$_4$—S)—T—D—A$_2$pr—I—C—E—NH$_2$ | 37 |
| YJ3(Et) | ++ | V—K—C(S—C$_2$H$_4$—S)—T—D—Ser—I—C—E—NH$_2$ | 38 |
| YJ4(Et) | +++ | Ac—V—K—C(S—C$_2$H$_4$—S)—T—D—Ser—I—C—E—NH$_2$ | 39 |
| YJ5(Et) | − | Suc—K—C(S—C$_2$H$_4$—S)—T—D—Ser—I—C—E—NH$_2$ | 40 |
| YJ6(Et) | − | V—K—C(S—C$_2$H$_4$—S)—T—D—Ser—I—C—E—NH$_2$ | 41 |
| YJ7(Et) | + | Ac—V—K—C(S—C$_2$H$_4$—S)—T—D—Ser—I—C—E—NH$_2$ | 42 |
| YJ8(Et) | − | V—K—C(S—C$_2$H$_4$—S)—T—Hfe—I—C—E—NH$_2$ | 43 |
| YJ9(Et) | +++ | Ac—V—K—C(S—C$_2$H$_4$—S)—T—Hfe—I—C—E—NH$_2$ | 44 |
| YJ10(lactam) | + | V—K—E((O)C—NH)—T—G—I—A$_2$bu—E—NH$_2$ | 45 |
| YJ11(lactam) | − | V—K—A$_2$bu(HN—C(O))—T—G—I—E—E—NH$_2$ | 46 |

-continued

| Name | Activity | Peptide Sequence | SEQ ID NO |
|---|---|---|---|
| YJ12(lactam) | + | Ac—V—K—E(—(O)C—NH—)—T—G—I—Orn(—NH—)—E—NH$_2$ | 47 |
| YJ13(lactam) | +++ | Ac—V—K—Orn(—HN—)—T—G—I—E(—C(O)—)—E—NH$_2$ | 48 |
| YJ2(SS) | + | Ac—V—K—C(—S—)—T—D•A$_2$pr—I—C(—S—)—E—NH$_2$ | 49 |
| YJ14(lactam) | +++ | Ac—V—K—E(—(O)C—HN—)—T—G—I—Lys(—)—E—NH$_2$ | 50 |
| YJ15(Et) | − | Ac—V—K—C(—S—C$_2$H$_4$—S—)—T—G—I—C—E—OH | 51 |
| Yja | +++ | Ac—V—K—C(—S—CH$_2$—S—)—T—G—I—C—E—NH$_2$ | 52 |
| Yjb | +++ | Ac—V—K—C(—S—S—)—T—G—I—C—E—NH$_2$ | 53 |

Abbreviations used in Table 3 are as follows:

| | |
|---|---|
| Ac: | Acetyl (denotes here acetylated α amine of the N-terminal Valine residue) |
| A$_2$bu: | 1,4 diamino butanoic acid. |
| A$_2$pr: | 1,3 diamino propanoic acid |
| Suc: | succinyl (denotes succinylated α amine of the N-terminal residue) |
| Hfe: | homophenylalanine |
| —OH: | a free carboxylic acid group at the carboxy terminal |
| —NH$_2$ | a carboxamide group at the carboxy terminal |
| Orn: | ornithine |
| CH$_2$: | methyl |
| C$_2$H$_4$: | ethyl |

Example 4

Inhibtion of RGS8-Mediated GTPase Acceleration

Figure 10:
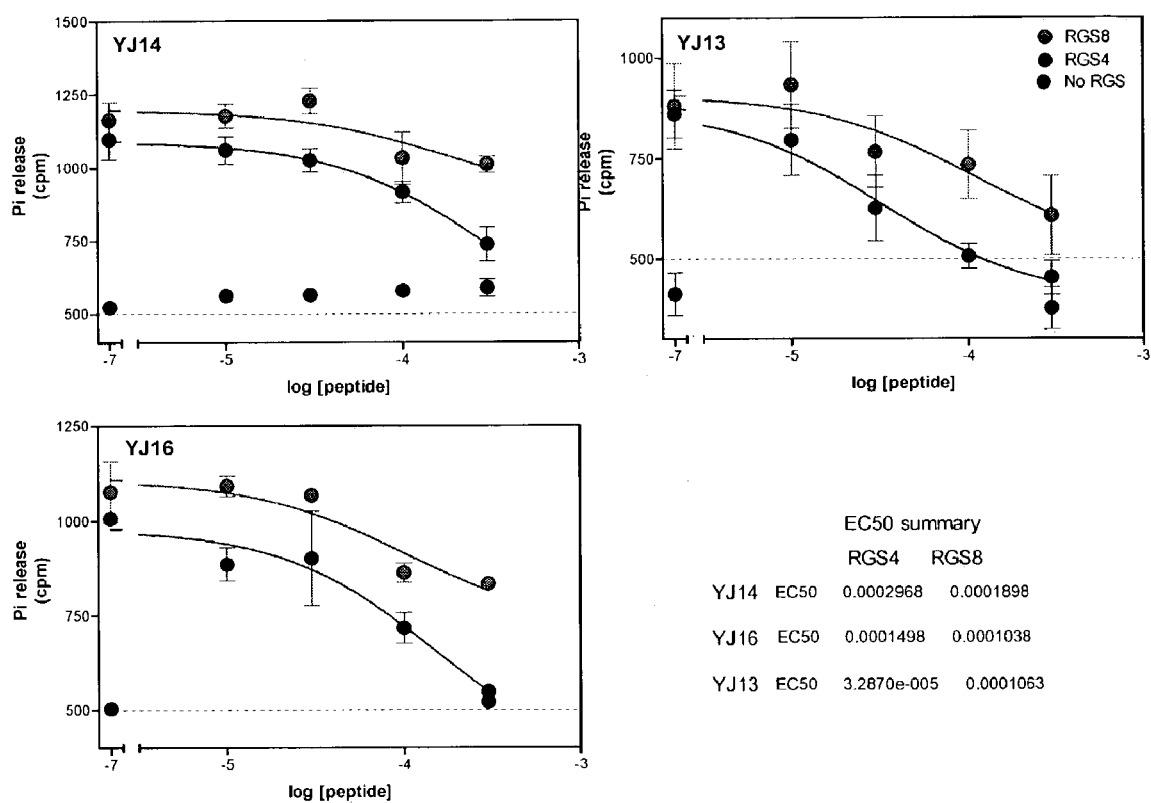
FIG. 10 illustrates the inhibitory activity of some of the peptides of the present invention against RGS4 and RGS8 stimulated GTPase activity.

In addition to the inhibitory activity against RGS4 mediated GTPase acceleration, three of the peptides found to be most inhibitory against RGS4 were tested for their ability to inhibit RGS8 stimulated GTPase activity. Each of the YJ13, YJ14, and YJ16 peptides were found to inhibit RGS8 stimulated GTPase activity (FIG. 10 and Table 4).

TABLE 4

Inhibitory potency of RGS inhibitor peptides at RGS4 and RGS8

| Peptide | IC$_{50}$ for RGS4 (μM) | IC$_{50}$ for RGS8 (μM) |
|---|---|---|
| YJ13 | 25 | 161 |
| YJ14 | 260 | 840 |
| YJ16 | 97 | 350 |
| JMRAC(Et) | 88 | ND |
| Yja | 79 | ND |
| Yjb | 26 | ND |

* ND = not determined

Figure 11:
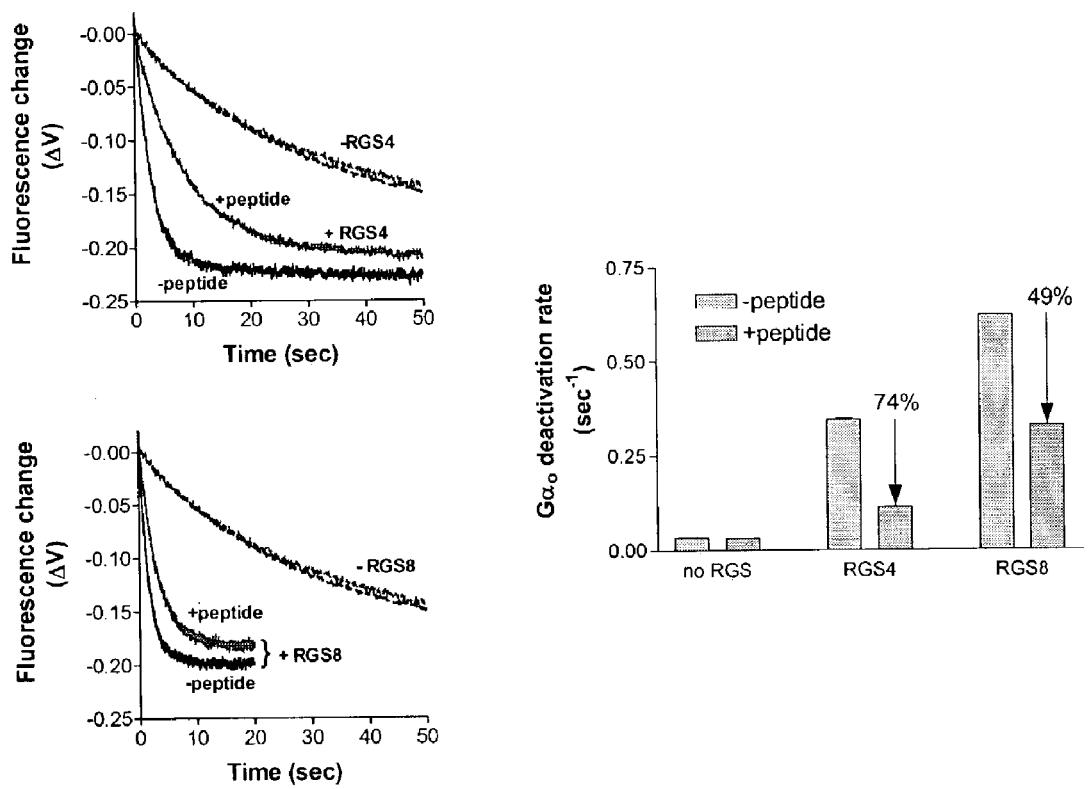
FIG. 11 shows spectroscopic single-turnover measurements of YJ13 inhibition of RGS4 and RGS8 stimulated GTP hydrolysis by purified $G\alpha_o$. Enhanced rates of $G\alpha$ deactivation in the presence of RGS4 or RGS8 are shown in panels A and B. The ability of the YJ13 peptide at 100 µM to inhibit the enhanced RGS deactivation is shown in panel C. The degree of inhibition in this assay with purified RGS and $G\alpha$ proteins confirms the $IC_{50}$ values defined in the steady-state membrane GTPase assays (Table 3). This data indicates that the peptide inhibition in membranes and with purified proteins is very similar and supports the use of the simpler steady-state membrane GTPase assay for evaluating RGS inhibitors.

In addition to the steady state GTPase assay with the receptor membrane system, the most potent peptide, YJ13, was also tested with purified Gα$_o$ and RGS4 and RGS8 in a spectroscopic single-turnover assay (Lan et al., 2001). This peptide inhibited RGS4 and RGS8 activity in this assay as well (FIG. 11). The degree of inhibition with purified proteins is entirely consistent with the IC$_{50}$ values derived from the membrane GTPase data.

Example 5

Fluorescent Assay for Inhibitors of RGS Proteins

This Example describes a fluorescence-based assay for inhibitors of RGS protein. Gα$_o$ (50 nM) and BODIPY GTPγS (50 nM) in HEM buffer (50 mM Hepes, 1 mM EDTA, 10 mM MgCl$_2$, pH 8) were incubated for various times at 25° C. Fluorescence was monitored every 10 minutes using fluorescein filters in a Victor 96-well plate reader. RGS proteins were added at various concentrations. RGS proteins were preincubated with any candidate inhibitor (or modulator), Gα$_o$ was added, and the binding reaction was initiation by the addition of BODIPY GTPγS at 25° C., followed by measurement of fluorescence every 10 minutes for 60-120 minutes.

The measure the effect of various perturbants, 100 mM NaCl, 10% glycerol, or 10% DMSO were tested in the BODIPY RGS assay. 300 nM GST-RGS8, 50 nM Gα$_o$, or 50 nM BODIPY were incubated for 120 minutes in the presence of the indicated perturbants.

Figure 15:
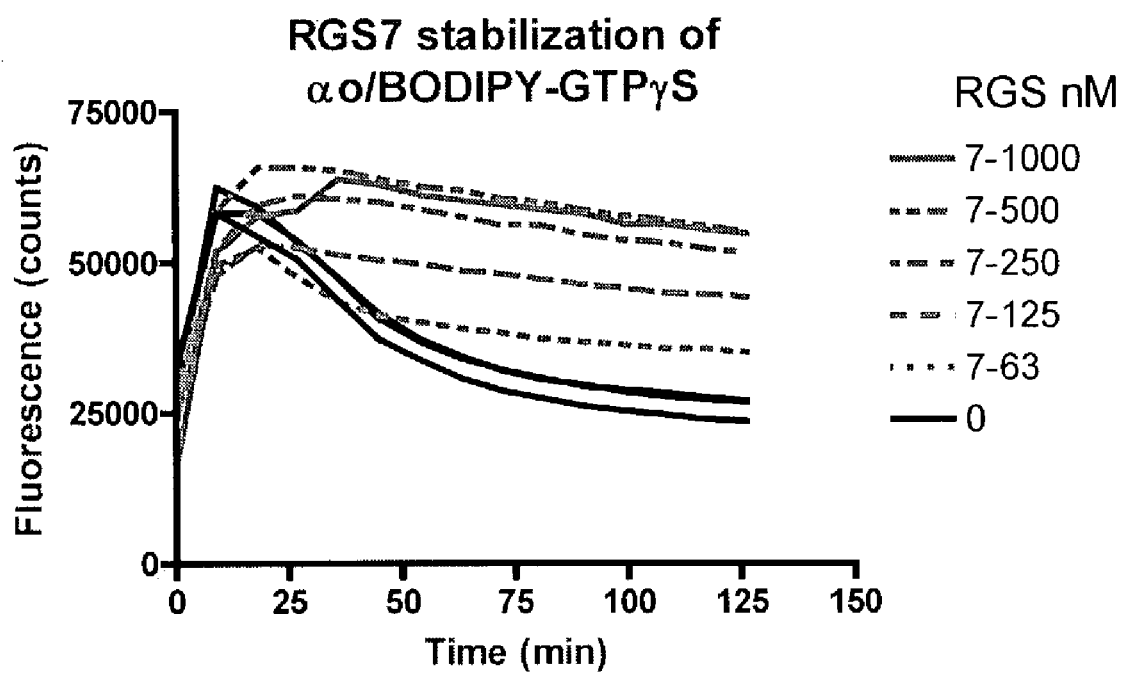
FIG. 15 shows a time course of BODIPY $G\alpha_o$ fluorescence with and without RGS7.

FIG. 15 shows a time course of BODIPY Gα$_o$ with and without RGS7. A biphasic kinetic curve for BODIPY fluorescence in the presence of Gα$_o$ was observed. Addition of RGS7 protein to the binding reaction greatly delayed the decrease in fluorescence leading to a 2-3 fold increase in fluorescence measured at longer times (60 minutes or greater). The fluorescence enhancement by the RGS protein is stable from 60 minutes to many hours of incubation.

Figure 16:
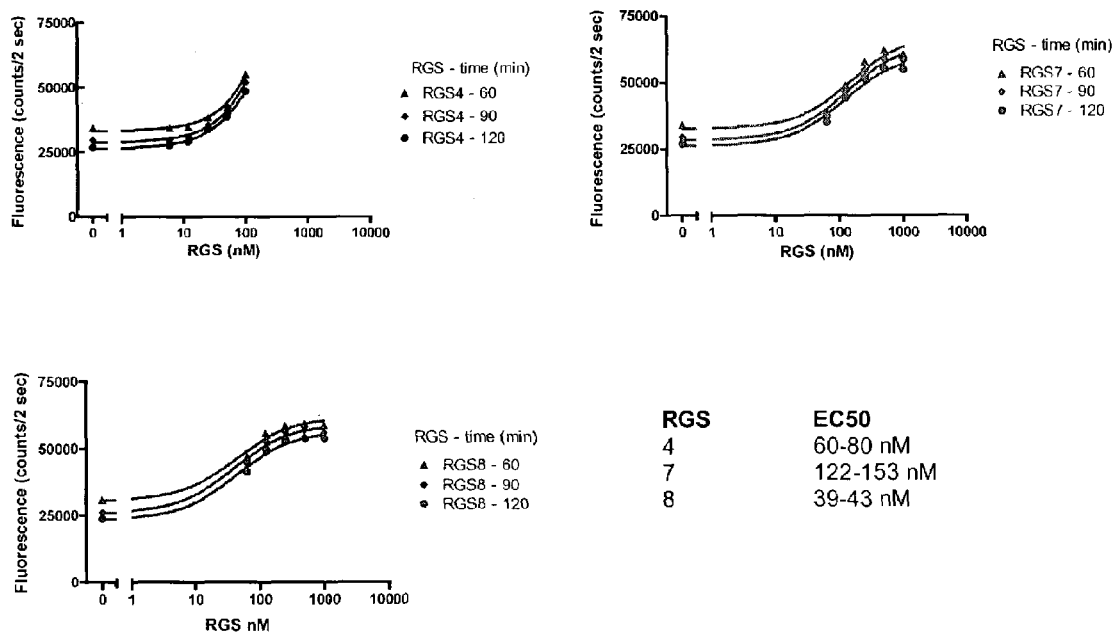
FIG. 16 shows RGS concentration dependence for BODIPY fluorescence enhancement.

FIG. 16 shows the RGS concentration dependence for BODIPY fluorescence enhancement. Data is shown for RGS4, 7, and 8 at various concentrations. The fluorescence enhancement is stable over time (with slightly greater fold-increases at the longer times).

Figure 17:
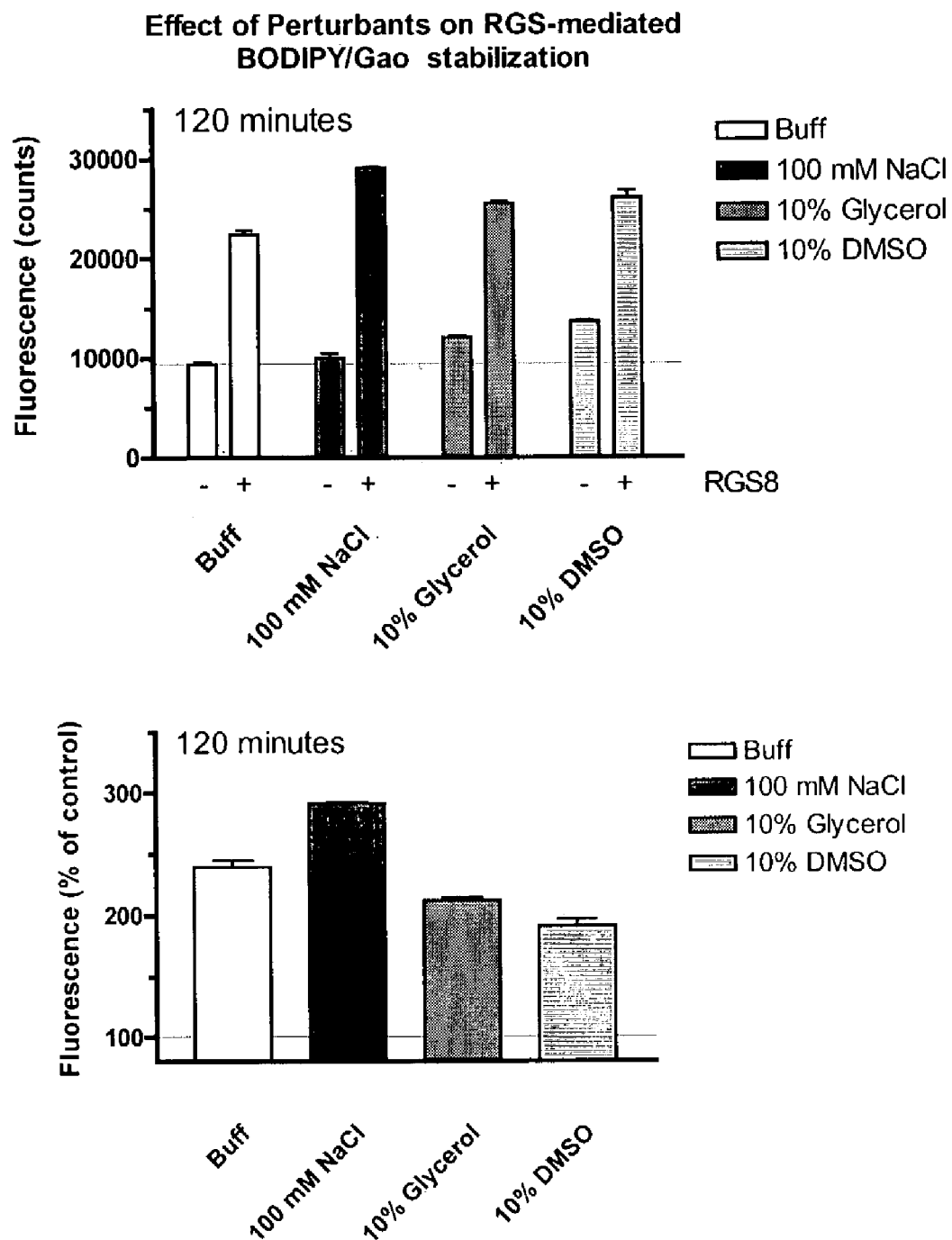
FIG. 17 shows the effect of perturbants on the fluorescent BODIPY/RGS assay used in some embodiments of the present invention.

FIG. 17 shows the effects of the perturbants on BODIPY/RGS assay. The effect of 100 mM NaCl, 10% glycerol and 10% DMSO were tested in the BODIPY RGS assay. 300 nM GST-RGS8, 50 nM Gα$_o$, and 50 nM BODIPY were incubated for 120 minutes in the presence of the indicated perturbants to determine whether the assay was influenced by common constituents. The assay was not inhibited by the tested perturbants.

Figure 18:
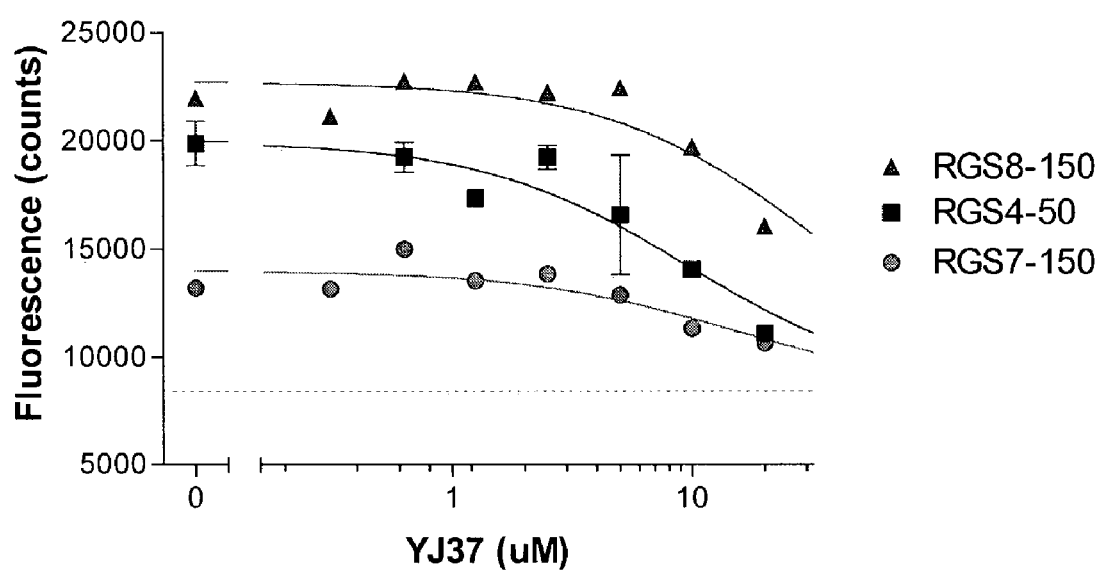
FIG. 18 shows inhibition of RGS stabilization of BODIPY $G\alpha_o$ by synthetic RGS inhibitor peptides of some embodiments of the present invention.

FIG. 18 shows the inhibition of RGS stabilization of BODIPY Gα$_o$, by synthetic RGS inhibitor peptides. Different concentrations of the three RGS proteins were incubated with YJ37 (See above Examples) at the indicated concentrations for 60 minutes at 25° C. Fluorescence was read in a 96-well plate reader and data plotted as log dose response curves. The fluorescence signal was lower in the presence of YJ37, indicating that the assay measures RGS inhibition by YJ37.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A constrained peptide, wherein said constrained peptide is selected from the group consisting of:

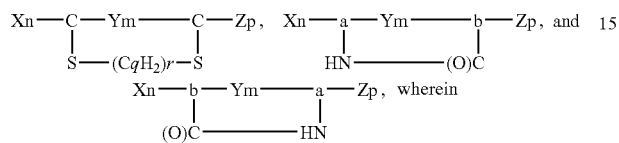

a is an amino acid with an amine side chain, b is an amino acid with a carboxyl side chain, and q is 1 and r is an integer between 0 and 10, and wherein Xn is V-K or Ac-V-K; wherein Zp is E; and wherein Ym is selected from the group consisting of: T-G-I, T-Hfe-I, T-G-F, T-(D-Ser)-I, and T-G-Y.

2. A constrained peptide, wherein said constrained peptide is selected from the group consisting of:

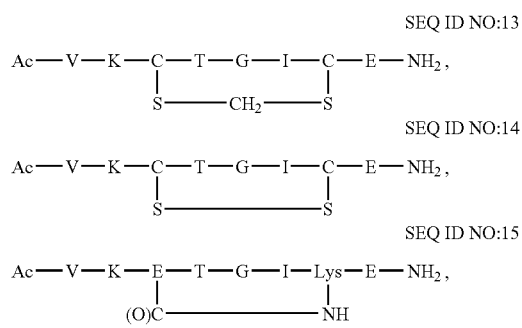

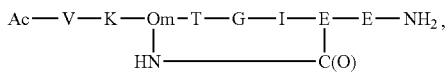

3. The constrained peptide of claim 1, wherein Xn comprises V-K.

4. The constrained peptide of claim 1, wherein Xn comprises Ac-V-K.

5. The constrained peptide of claim 1, wherein a is 1,4 diamino butanoic acid.

6. The constrained peptide of claim 1, wherein a is ornithine.

7. The constrained peptide of claim 1, wherein a is lysine.

8. The constrained peptide of claim 1, wherein b is glutamate.

9. The constrained peptide of claim 1, wherein Ym is T-G-I.

10. The constrained peptide of claim 1, wherein Ym is T-Hfe-I.

11. The constrained peptide of claim 1, wherein Ym is T-G-F.

12. The constrained peptide of claim 1, wherein Ym is T-(D-Ser)-I.

13. The constrained peptide of claim 1, wherein Ym is T-G-Y.

* * * * *

```
                        SEQUENCE LISTING

<160> NUMBER OF SEQ ID NOS: 53

<210> SEQ ID NO 1
    <211> LENGTH: 7
    <212> TYPE: PRT
    <213> ORGANISM: Artificial Sequence
    <220> FEATURE:
    <223> OTHER INFORMATION: Synthetic

<400> SEQUENCE: 1

Lys Thr Thr Gly Ile Val Glu
    1               5

<210> SEQ ID NO 2
    <211> LENGTH: 8
    <212> TYPE: PRT
    <213> ORGANISM: Artificial Sequence
    <220> FEATURE:
    <223> OTHER INFORMATION: Synthetic

<400> SEQUENCE: 2

Val Lys Thr Thr Gly Ile Val Glu
    1               5

<210> SEQ ID NO 3
    <211> LENGTH: 8
    <212> TYPE: PRT
    <213> ORGANISM: Artificial Sequence
    <220> FEATURE:
    <223> OTHER INFORMATION: Synthetic

<400> SEQUENCE: 3

Val Lys Thr Thr Gly Ile Ile Glu
    1               5

<210> SEQ ID NO 4
    <211> LENGTH: 8
    <212> TYPE: PRT
    <213> ORGANISM: Artificial Sequence
    <220> FEATURE:
    <223> OTHER INFORMATION: Synthetic

<400> SEQUENCE: 4

Asp Met Thr Thr Gly Ile Val Glu
    1               5

<210> SEQ ID NO 5
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 5

Val Pro Thr Thr Gly Ile Ile Glu
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Met Pro Thr Thr Gly Ile Asn Glu
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic

<400> SEQUENCE: 7

Lys Ala Thr Lys Gly Ile Val Glu
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Arg Pro Thr Lys Gly Ile His Glu
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Val Leu Thr Ser Gly Ile Phe Glu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: This cysteine is connected by a linker to
      cysteine at position 7.
```

```
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: This cysteine is connected by a linker to
      cysteine at position 3.

<400> SEQUENCE: 10

Xaa Xaa Cys Xaa Gly Ile Cys Glu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: This can be any amino acid with an amine side
      chain connected by a linker to an amino acid with a carboxyl
      side chain at position 7.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: This can be any amino acid with a carboxyl side
      chain connected by a linker to an amino acid with an amine side
      chain at position 3.

<400> SEQUENCE: 11

Xaa Xaa Xaa Xaa Gly Ile Xaa Glu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: This is any amino acid with a carboxyl side
      chain connected by a linker to an amino acid with an amine side
      chain at position 7.
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: This is any amino acid with an amine side
      chain connected by a linker to a carboxyl side chain at position
      3.

<400> SEQUENCE: 12

Xaa Xaa Xaa Xaa Gly Ile Xaa Glu
```

-continued

```
<210> SEQ ID NO 13
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the  N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 13

Val Lys Cys Thr Gly Ile Cys Glu
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the  N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 14

Val Lys Cys Thr Gly Ile Cys Glu
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
```

```
      Valine residue.
<220> FEATURE:
<221> NAME/KEY: MISC_FEATURE
<222> LOCATION: (3)..(3)
<223> OTHER INFORMATION: The glutamic acid is connected by a linker to
      lysine at position 7.
<220> FEATURE:
<221> NAME/KEY: MISC_FEATURE
<222> LOCATION: (7)..(7)
<223> OTHER INFORMATION: The lysine is connected by a linker to
      glutamic acid at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 15

Val Lys Glu Thr Gly Ile Lys Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MOD_RES
<222> LOCATION: (3)..(3)
<223> OTHER INFORMATION: Orn is connected by a linker to glutamic acid
      at position 7.
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Glutamic acid is connected by a linker to
      ornithine at position ornithine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 16

Val Lys Xaa Thr Gly Ile Glu Glu
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
```

```
<223> OTHER INFORMATION: Homophenylalanine
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 17

Val Lys Cys Thr Xaa Ile Cys Glu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 18

Val Lys Cys Thr Gly Phe Cys Glu
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to a
      cysteine at position 7.
<220> FEATURE:
<221> NAME/KEY: MISC_FEATURE
<222> LOCATION: (7)..(7)
<223> OTHER INFORMATION: This cysteine is connected by a linker to a
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 19
```

```
Val Lys Cys Thr Gly Ile Cys Glu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: D-Ser
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 20

Val Lys Cys Thr Ser Ile Cys Glu
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.

<400> SEQUENCE: 21

Val Lys Cys Thr Gly Ile Cys Glu
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
```

```
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Xaa Xaa Thr Xaa Gly Ile Xaa Glu
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 23

Xaa Xaa Cys Xaa Gly Ile Cys Glu
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 24

Val Lys Cys Thr Gly Ile Cys Glu
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
```

```
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 25

Val Lys Cys Thr Gly Ile Cys Glu
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (4)..(4)
<223> OTHER INFORMATION: 1,4 diamino butanoic acid
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 26

Val Lys Cys Xaa Gly Ile Cys Glu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (4)..(4)
<223> OTHER INFORMATION: 1,4 diamino butanoic acid
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 27
```

```
Val Lys Cys Xaa Gly Ile Cys Glu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (4)..(4)
<223> OTHER INFORMATION: 1,3 diamino propanoic acid
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 28

Val Lys Cys Xaa Gly Ile Cys Glu
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (4)..(4)
<223> OTHER INFORMATION: 1,3 diamino propanoic acid
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 29

Val Lys Cys Xaa Gly Ile Cys Glu
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid at this position is attached to
      a carboxamide group at the carboxy terminal.

<400> SEQUENCE: 30

Val Lys Cys Thr Gly Phe Cys Glu
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 31

Val Lys Cys Thr Gly Phe Cys Glu
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 8.
<220> FEATURE:
<221> NAME/KEY: MISC_FEATURE
<222> LOCATION: (6)..(6)
<223> OTHER INFORMATION: 1,4 diamino butanoic acid
<220> FEATURE:
<221> NAME/KEY: MISC_FEATURE
<222> LOCATION: (8)..(8)
<223> OTHER INFORMATION: This cysteine is connected by a linker to
      cysteine at position 3.
<220> FEATURE:
<221> NAME/KEY: MISC_FEATURE
<222> LOCATION: (9)..(9)
<223> OTHER INFORMATION: Glutamic acid is attached to a carboxamide
``` group at the carboxy terminal.

<400> SEQUENCE: 32

Val Lys Cys Thr Asp Xaa Ile Cys Glu
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 8.
<220> FEATURE:
<221> NAME/KEY: MISC_FEATURE
<222> LOCATION: (6)..(6)
<223> OTHER INFORMATION: 1,4 diamino butanoic acid
<220> FEATURE:
<221> NAME/KEY: MISC_FEATURE
<222> LOCATION: (8)..(8)
<223> OTHER INFORMATION: This cysteine is connected by a linker to
      cysteine at position 3.
<220> FEATURE:
<221> NAME/KEY: MISC_FEATURE
<222> LOCATION: (9)..(9)
<223> OTHER INFORMATION: Glutamic acid is attached to a carboxamide
      group at the carboxy terminal.

<400> SEQUENCE: 33

Val Lys Cys Thr Asp Xaa Ile Cys Glu
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 34

Val Lys Cys Thr Gly Tyr Cys Glu
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: Acetytalated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 35

Val Lys Cys Thr Gly Tyr Cys Glu
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 8.
<220> FEATURE:
<221> NAME/KEY: MISC_FEATURE
<222> LOCATION: (6)..(6)
<223> OTHER INFORMATION: 1,3 diamino propanoic acid
<220> FEATURE:
<221> NAME/KEY: MISC_FEATURE
<222> LOCATION: (8)..(8)
<223> OTHER INFORMATION: This cysteine is connected by a linker to
      cysteine at position 3.
<220> FEATURE:
<221> NAME/KEY: MISC_FEATURE
<222> LOCATION: (9)..(9)
<223> OTHER INFORMATION: Glutamic acid is attached to a carboxamide
      group at the carboxy terminal.

<400> SEQUENCE: 36

Val Lys Cys Thr Asp Xaa Ile Cys Glu
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 8.
<220> FEATURE:
<221> NAME/KEY: MISC_FEATURE
<222> LOCATION: (6)..(6)
<223> OTHER INFORMATION: 1,4 diamino butanoic acid
```

```
<220> FEATURE:
<221> NAME/KEY: MISC_FEATURE
<222> LOCATION: (8)..(8)
<223> OTHER INFORMATION: This cysteine is connected by a linker to
      cysteine at position 3.
<220> FEATURE:
<221> NAME/KEY: MISC_FEATURE
<222> LOCATION: (9)..(9)
<223> OTHER INFORMATION: Glutamic acid is attached to a carboxamide
      group at the carboxy terminal.

<400> SEQUENCE: 37

Val Lys Cys Thr Asp Xaa Ile Cys Glu
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: D-Ser
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 38

Val Lys Cys Thr Ser Ile Cys Glu
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: D-Ser
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.
```

```
<400> SEQUENCE: 39

Val Lys Cys Thr Ser Ile Cys Glu
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Succinylated alpha amine of the N-terminal
      residue.
<220> FEATURE:
<221> NAME/KEY: MISC_FEATURE
<222> LOCATION: (2)..(2)
<223> OTHER INFORMATION: This cysteine is connected by a linker to
      cysteine at position 6.
<220> FEATURE:
<221> NAME/KEY: MISC_FEATURE
<222> LOCATION: (4)..(4)
<223> OTHER INFORMATION: D-Ser
<220> FEATURE:
<221> NAME/KEY: MISC_FEATURE
<222> LOCATION: (6)..(6)
<223> OTHER INFORMATION: This cysteine is connected by a linker to
      cysteine at position 2.
<220> FEATURE:
<221> NAME/KEY: MISC_FEATURE
<222> LOCATION: (7)..(7)
<223> OTHER INFORMATION: Gluatamic acid is attached to a carboxamide
      group at the carboxy terminal.

<400> SEQUENCE: 40

Lys Cys Thr Ser Ile Cys Glu
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: D-Ser
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 41

Val Lys Cys Thr Ser Ile Cys Glu
1               5

<210> SEQ ID NO 42
<211> LENGTH: 8
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: D-Ser
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 42

Val Lys Cys Thr Ser Ile Cys Glu
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: Homophenylalanine
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 43

Val Lys Cys Thr Xaa Ile Cys Glu
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
```

```
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (5)..(5)
<223> OTHER INFORMATION: Homophenylalanine
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Gluatamic acid is attached to a carboxamide
      group at the carboxy terminal.

<400> SEQUENCE: 44

Val Lys Cys Thr Xaa Ile Cys Glu
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Glutamic acid is connected by a linker to 1,4
      diamino butanoic acid at position 7.
<220> FEATURE:
<221> NAME/KEY: MISC_FEATURE
<222> LOCATION: (7)..(7)
<223> OTHER INFORMATION: 1,4 diamino butanoic acid is connected by a
      linker to glutamic acid at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 45

Val Lys Glu Thr Gly Ile Xaa Glu
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: 1,4 diamino butanoic acid is connected by a
      linker to glutamic acid at position 7.
<220> FEATURE:
<221> NAME/KEY: MISC_FEATURE
<222> LOCATION: (7)..(7)
<223> OTHER INFORMATION: Glutamic acid is connected by a linker to 1,4
      diamino butanoic acid at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 46

Val Lys Xaa Thr Gly Ile Glu Glu
1               5
```

```
<210> SEQ ID NO 47
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: Glutamic acid is connected by a linker to
      ornithine at position 7.
<220> FEATURE:
<221> NAME/KEY: MOD_RES
<222> LOCATION: (7)..(7)
<223> OTHER INFORMATION: Orn
<220> FEATURE:
<221> NAME/KEY: MISC_FEATURE
<222> LOCATION: (7)..(7)
<223> OTHER INFORMATION: Ornithine is connected by a linker to
      glutamic acid at position 3.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 47

Val Lys Glu Thr Gly Ile Xaa Glu
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MOD_RES
<222> LOCATION: (3)..(3)
<223> OTHER INFORMATION: Orn
<220> FEATURE:
<221> NAME/KEY: MISC_FEATURE
<222> LOCATION: (3)..(3)
<223> OTHER INFORMATION: Ornithine is connected by a linker to
      gluatamic acid at position 7.
<220> FEATURE:
<221> NAME/KEY: MISC_FEATURE
<222> LOCATION: (7)..(7)
<223> OTHER INFORMATION: Glutamic acid is connected by a linker to
      ornithine at position 7.
<220> FEATURE:
<221> NAME/KEY: MISC_FEATURE
<222> LOCATION: (8)..(8)
<223> OTHER INFORMATION: Glutamic acid is attached to a carboxamide
      group at the carboxy terminal.

<400> SEQUENCE: 48

Val Lys Xaa Thr Gly Ile Glu Glu
1               5

<210> SEQ ID NO 49
<211> LENGTH: 9
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 8.
<220> FEATURE:
<221> NAME/KEY: MISC_FEATURE
<222> LOCATION: (6)..(6)
<223> OTHER INFORMATION: 1,3 diamino propanoic acid
<220> FEATURE:
<221> NAME/KEY: MISC_FEATURE
<222> LOCATION: (8)..(8)
<223> OTHER INFORMATION: This cysteine is connected by a linker to
      cysteine at position 3.
<220> FEATURE:
<221> NAME/KEY: MISC_FEATURE
<222> LOCATION: (9)..(9)
<223> OTHER INFORMATION: Gluatamic acid is attached to a carboxamide
      group at the carboxy terminal.

<400> SEQUENCE: 49

Val Lys Cys Thr Asp Xaa Ile Cys Glu
1               5

<210> SEQ ID NO 50
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: Glutamic acid is connected by a linker to
      lysine at position 7.
<220> FEATURE:
<221> NAME/KEY: MISC_FEATURE
<222> LOCATION: (7)..(7)
<223> OTHER INFORMATION: Lysine is connected by a linker to gluatamic
      acid at position 3.
<220> FEATURE:
<221> NAME/KEY: MISC_FEATURE
<222> LOCATION: (8)..(8)
<223> OTHER INFORMATION: Gluatamic acid is attached to a carboxamide
      group at the carboxy terminal.

<400> SEQUENCE: 50

Val Lys Glu Thr Gly Ile Lys Glu
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
```

```
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Gluatamic acid is attached to a carboxamide
      group at the carboxy terminal.

<400> SEQUENCE: 51

Val Lys Cys Thr Gly Ile Cys Glu
1               5

<210> SEQ ID NO 52
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Gluatamic acid is attached to a carboxamide
      group at the carboxy terminal.

<400> SEQUENCE: 52

Val Lys Cys Thr Gly Ile Cys Glu
1               5

<210> SEQ ID NO 53
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Acetylated alpha amine of the N-terminal
      Valine residue.
<220> FEATURE:
<221> NAME/KEY: MISC_FEATURE
<222> LOCATION: (3)..(3)
<223> OTHER INFORMATION: This cysteine is connected by a linker to
      cysteine at position 7.
<220> FEATURE:
<221> NAME/KEY: MISC_FEATURE
<222> LOCATION: (7)..(7)
<223> OTHER INFORMATION: This cysteine is connected by a linker to
      cysteine at position 3.
<220> FEATURE:
<221> NAME/KEY: MISC_FEATURE
<222> LOCATION: (8)..(8)
<223> OTHER INFORMATION: Gluatamic acid is attached to a carboxamide
      group at the carboxy terminal.
```

```
<400> SEQUENCE: 53

Val Lys Cys Thr Gly Ile Cys Glu
1               5
```